(12) United States Patent
Miyasato et al.

(10) Patent No.: US 10,323,050 B2
(45) Date of Patent: Jun. 18, 2019

(54) NON-AQUEOUS ELECTROLYTE SOLUTION FOR BATTERY, NOVEL COMPOUND, POLYELECTROLYTE, AND LITHIUM SECONDARY BATTERY

(71) Applicant: MITSUI CHEMICALS, INC., Minato-ku, Tokyo (JP)

(72) Inventors: Masataka Miyasato, Sodegaura (JP); Satoko Fujiyama, Kisarazu (JP); Takashi Hayashi, Ichihara (JP); Takeshi Kobayashi, Chiba (JP)

(73) Assignee: MITSUI CHEMICALS, INC., Minato-Ku, Tokyo (JP)

( * ) Notice: Subject to any disclaimer, the term of this patent is extended or adjusted under 35 U.S.C. 154(b) by 894 days.

(21) Appl. No.: 14/779,716

(22) PCT Filed: Apr. 21, 2014

(86) PCT No.: PCT/JP2014/061190
§ 371 (c)(1),
(2) Date: Sep. 24, 2015

(87) PCT Pub. No.: WO2014/175225
PCT Pub. Date: Oct. 30, 2014

(65) Prior Publication Data
US 2016/0108070 A1 Apr. 21, 2016

(30) Foreign Application Priority Data
Apr. 25, 2013 (JP) .................. 2013-092924

(51) Int. Cl.
*H01M 10/0567* (2010.01)
*C07F 9/06* (2006.01)
(Continued)

(52) U.S. Cl.
CPC .............. *C07F 9/06* (2013.01); *C01D 15/00* (2013.01); *C07F 9/092* (2013.01); *C07F 9/4071* (2013.01);
(Continued)

(58) Field of Classification Search
None
See application file for complete search history.

(56) References Cited

U.S. PATENT DOCUMENTS 3,910,878 A * 10/1975 McAda ................. C07F 9/141
536/1.11
4,226,840 A * 10/1980 Fieldhouse ........... C01B 21/098
423/300
(Continued)

FOREIGN PATENT DOCUMENTS

JP 11-149943 A 6/1999
JP 2966451 B2 10/1999
(Continued)

OTHER PUBLICATIONS

International Search Report (PCT/ISA/210) dated Jul. 1, 2014, by the Japanese Patent Office as the International Searching Authority for International Application No. PCT/JP2014/061190.
(Continued)

*Primary Examiner* — Jeremiah R Smith
(74) *Attorney, Agent, or Firm* — Buchanan, Ingersoll & Rooney PC

(57) ABSTRACT

A non-aqueous electrolyte solution for a battery, including a compound represented by formula (1), wherein each A represents P or P=O; each R represents H, a halogen, an alkyl, an aryl, an alkoxy or an aryloxy; each X represents H, an alkyl, an aryl, an alkali metal or formula (2); each Y represents H, a halogen, an alkyl, an aryl, an alkoxy, an aryloxy or formula (3); each Z represents H, an alkyl, an aryl or $OZ^1$; $Z^1$ represents H, an alkyl, an aryl, an alkali metal, formula (2), or formula (4); each M represents an alkali metal; n is 1 or more; m is 1 or more; l is 1 or more; a sum of n, m and l in one molecule is from 1 to 200; and each * represents a position of bonding:

(Continued)

US 10,323,050 B2
Page 2

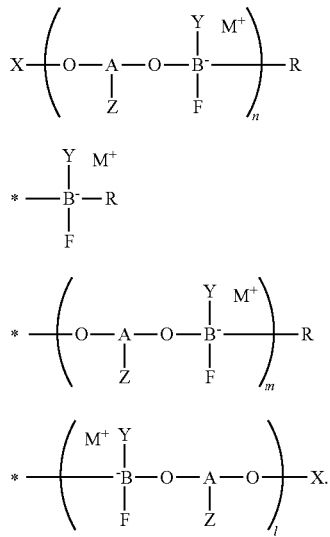

17 Claims, 1 Drawing Sheet

(51) Int. Cl.
| | |
|---|---|
| *C07F 9/09* | (2006.01) |
| *C07F 9/40* | (2006.01) |
| *C01D 15/00* | (2006.01) |
| *H01M 4/587* | (2010.01) |
| *H01M 10/052* | (2010.01) |
| *H01M 10/0565* | (2010.01) |
| *H01M 10/056* | (2010.01) |
| *C01B 35/14* | (2006.01) |
| *H01M 10/0568* | (2010.01) |
| *H01M 4/02* | (2006.01) |

(52) U.S. Cl.
CPC ......... *H01M 4/587* (2013.01); *H01M 10/052* (2013.01); *H01M 10/0565* (2013.01); *H01M 10/0567* (2013.01); *C01B 35/14* (2013.01); *H01M 10/056* (2013.01); *H01M 10/0568* (2013.01); *H01M 2004/027* (2013.01); *H01M 2220/20* (2013.01); *H01M 2220/30* (2013.01); *H01M 2300/0017* (2013.01); *H01M 2300/0025* (2013.01); *H01M 2300/0085* (2013.01); *Y02T 10/7011* (2013.01)

(56) References Cited

U.S. PATENT DOCUMENTS

| | | | |
|---|---|---|---|
| 6,045,948 A | | 4/2000 | Wang et al. |
| 2006/0068295 A1* | | 3/2006 | Xu .................. H01M 6/164 429/322 |
| 2009/0325065 A1* | | 12/2009 | Fujii ................. H01M 4/04 429/199 |
| 2011/0111289 A1* | | 5/2011 | Choi ................. H01M 4/131 429/207 |
| 2012/0028132 A1 | | 2/2012 | Tsujioka et al. |
| 2012/0237836 A1* | | 9/2012 | Kim .................. H01M 10/525 429/336 |
| 2014/0125292 A1* | | 5/2014 | Best .................. H01M 10/0525 320/137 |
| 2017/0040649 A1* | | 2/2017 | Schmitz ............ H01M 10/052 |

FOREIGN PATENT DOCUMENTS

| | | |
|---|---|---|
| JP | 2004-031079 A | 1/2004 |
| JP | 2010-257616 A | 11/2010 |
| JP | 2013-035695 A | 2/2013 |
| WO | WO 98/07729 A1 | 2/1998 |

OTHER PUBLICATIONS

Written Opinion (PCT/ISA/237) dated Jul. 1, 2014, by the Japanese Patent Office as the International Searching Authority for International Application No. PCT/JP2014/061190.

\* cited by examiner

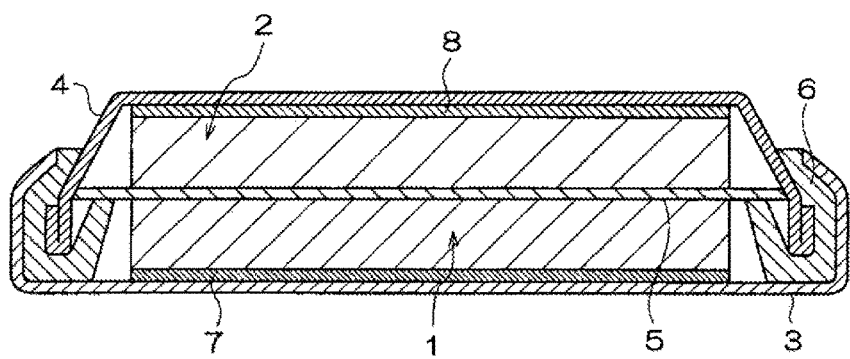

NON-AQUEOUS ELECTROLYTE SOLUTION FOR BATTERY, NOVEL COMPOUND, POLYELECTROLYTE, AND LITHIUM SECONDARY BATTERY

TECHNICAL FIELD

The present invention relates to a non-aqueous electrolyte solution for a battery, a novel compound, a polyelectrolyte, and a lithium secondary battery that can be charged and discharged and that be used, for example, for a power source of a portable electric instrument, for adapting for car, or for electric power storage.

BACKGROUND ART

In recent years, lithium secondary batteries are widely used as power sources for electronic devices such as portable telephones and notebook computers, or for electric cars or electric power storage. Particularly recently, there is a rapidly increasing demand for a high capacity and high power battery with a high energy density, which can be mounted in hybrid cars or electric cars.

Lithium secondary batteries are primarily composed of a positive electrode and a negative electrode, which contain materials capable of absorption and desorption of lithium, and a non-aqueous electrolyte solution containing a lithium salt and a non-aqueous solvent.

Examples of positive electrode active materials used in a positive electrode include lithium metal oxides such as $LiCoO_2$, $LiMnO_2$, $LiNiO_2$, and $LiFePO_4$.

Furthermore, as the non-aqueous electrolyte solution, solutions prepared by mixing a mixed solvent (non-aqueous solvent) of carbonates such as ethylene carbonate or propylene carbonate, with a Li electrolyte such as $LiPF_6$, $LiBF_4$, $LiN(SO_2CF_3)_2$ or $LiN(SO_2CF_2CF_3)_2$, are used.

On the other hand, as the active material for a negative electrode that is used in negative electrodes, metal lithium, metal compounds (elemental metals, oxides, alloys with lithium, and the like) capable of absorption and desorption of lithium, and carbon materials are known. Particularly, lithium secondary batteries employing cokes, artificial graphite or natural graphite, which are all capable of absorption and desorption of lithium, have been put to practical use.

As an attempt for improving battery performances, for example, a technique is suggested in which a compound containing phosphorus (P) and boron (B) as constituent elements is incorporated into a non-aqueous electrolyte solution (see, for example, Japanese Patent Application Laid-Open (JP-A) No. 2010-257616).

An electrolytic capacitor using a borate compound containing a phosphorus element is also suggested (see, for example, Japanese Patent No. 2966451).

SUMMARY OF INVENTION

Technical Problem

Although JP-A No. 2010-257616 describes characteristics of the battery after the battery undergoes charge and discharge cycles, an initial resistance characteristic of the battery is not improved. Thus, the battery needs to be further improved. About Japanese Patent No. 2966451, an investigation has not been made at all about the application of the phosphorus-element-containing borate compound to any battery (for example, a lithium secondary battery).

The invention has been made to cope with the problems, and an object of the invention is to provide a non-aqueous electrolyte solution for a battery, a novel compound and a polyelectrolyte that can each improve an initial resistance characteristic of a battery, and to provide a lithium secondary battery with an improved initial resistance characteristic.

Solution to Problem

The inventors diligently studied the problem described above, and have found out that an initial resistance characteristic of a battery can be improved by adding a specific compound to a non-aqueous electrolyte solution for the battery, and have thus accomplished the invention.

That is, means for solving the problem are as follows.

<1> A non-aqueous electrolyte solution for a battery, comprising a compound represented by the following formula (1):

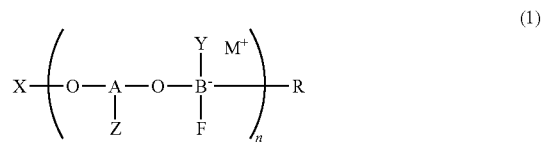

(1)

(2)

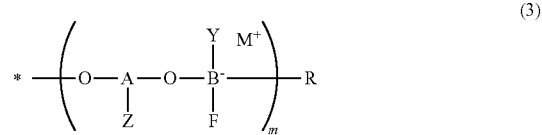

(3)

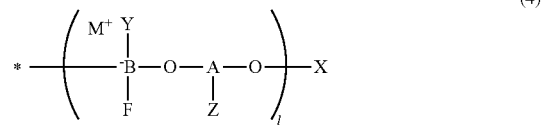

(4)

wherein in formulae (1) to (4), each A represents a phosphorus atom or P=O; each R represents a hydrogen atom, a halogen atom, an alky group, an aryl group, an alkoxy group, or an aryloxy group; each X represents a hydrogen atom, an alkyl group, an aryl group, an alkali metal atom, or a group represented by formula (2); each Y represents a hydrogen atom, a halogen atom, an alkyl group, an aryl group, an alkoxy group, an aryloxy group, or a group represented by formula (3); each Z represents a hydrogen atom, an alkyl group, an aryl group, or an $OZ^1$ group wherein $Z^1$ represents a hydrogen atom, an alkyl group, an aryl group, an alkali metal atom, a group represented by formula (2), or a group represented by formula (4); each M represents an alkali metal atom; n represents an integer of 1 or more, m represents an integer of 1 or more, and l represents an integer of 1 or more, provided that a sum of n, m, and l in one molecule of the compound represented by formula (1) is an integer from 1 to 200; and in formulae (2) to (4), each * represents a position of bonding.

<2> The non-aqueous electrolyte solution for a battery according to <1>, wherein each of A in formula (1), A in formula (3), and A in formula (4) is P=O.

<3> The non-aqueous electrolyte solution for a battery according to <1> or <2>, wherein the sum of n, m, and l in one molecule of the compound represented by formula (1) is an integer from 1 to 30.

<4> The non-aqueous electrolyte solution for a battery according to any one of <1> to <3>, wherein n in formula (1) is an integer from 1 to 10; and each of Y in formula (1) and Y in formula (2) is independently a hydrogen atom, a halogen atom, an alkyl group, aryl group, an alkoxy group, or an aryloxy group; and Z in formula (1) is a hydrogen atom, an alkyl group, an aryl group, or an $OZ^1$ group wherein $Z^1$ is a hydrogen atom, an alkyl group, an aryl group, an alkali metal atom, or a group represented by formula (2).

<5> The non-aqueous electrolyte solution for a battery according to any one of <1> to <4>, wherein each of Z in formula (1), Z in formula (3), and Z in formula (4) is the $OZ^1$ group.

<6> A compound represented by the following formula (1):

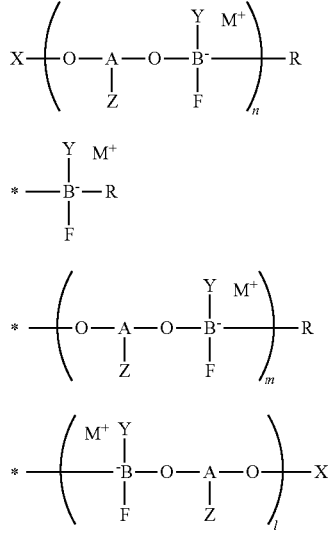

wherein in formulae (1) to (4), each A represents a phosphorus atom or P=O; each R represents a hydrogen atom, a halogen atom, an alky group, an aryl group, an alkoxy group, or an aryloxy group; each X represents a hydrogen atom, an alkyl group, an aryl group, an alkali metal atom, or a group represented by formula (2); each Y represents a hydrogen atom, a halogen atom, an alkyl group, an aryl group, an alkoxy group, an aryloxy group, or a group represented by formula (3); each Z represents a hydrogen atom, an alkyl group, an aryl group, or an $OZ^1$ group wherein $Z^1$ represents a hydrogen atom, an alkyl group, an aryl group, an alkali metal atom, a group represented by formula (2), or a group represented by formula (4); each M represents an alkali metal atom; n represents an integer of 1 or more, m represents an integer of 1 or more, and l represents an integer of 1 or more, provided that a sum of n, m, and l in one molecule of the compound represented by formula (1) is an integer from 1 to 200; and in formulae (2) to (4), each * represents a position of bonding.

<7> The compound according to <6>, wherein each of A in formula (1), A in formula (3), and A in formula (4) is P=O.

<8> The compound according to <6> or <7>, wherein the sum of n, m, and l in one molecule of the compound is an integer from 1 to 30.

<9> The compound according to any one of <6> to <8>, wherein n in formula (1) is an integer from 1 to 10; and each of Y in formula (1) and Y in formula (2) is independently a hydrogen atom, a halogen atom, an alkyl group, aryl group, an alkoxy group, or an aryloxy group; and Z in formula (1) is a hydrogen atom, an alkyl group, an aryl group, or an $OZ^1$ group wherein $Z^1$ is a hydrogen atom, an alkyl group, an aryl group, an alkali metal atom, or a group represented by formula (2).

<10> The compound according to any one of <6> to <9>, wherein each of Z in formula (1), Z in formula (3), and Z in formula (4) is the $OZ^1$ group.

<11> A polyelectrolyte, comprising a compound represented by the following formula (1):

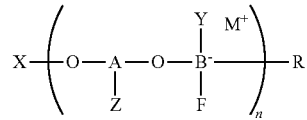
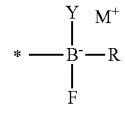
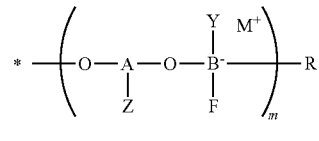
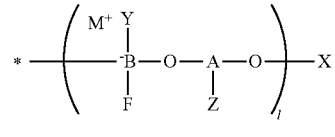

wherein in formulae (1) to (4), each A represents a phosphorus atom or P=O; each R represents a hydrogen atom, a halogen atom, an alky group, an aryl group, an alkoxy group, or an aryloxy group; each X represents a hydrogen atom, an alkyl group, an aryl group, an alkali metal atom, or a group represented by formula (2); each Y represents a hydrogen atom, a halogen atom, an alkyl group, an aryl group, an alkoxy group, an aryloxy group, or a group represented by formula (3); each Z represents a hydrogen atom, an alkyl group, an aryl group, or an $OZ^1$ group wherein $Z^1$ represents a hydrogen atom, an alkyl group, an aryl group, an alkali metal atom, a group represented by formula (2), or a group represented by formula (4); each M represents an alkali metal atom; n represents an integer of 1 or more, m represents an integer of 1 or more, and l represents an integer of 1 or more, provided that a sum of n, m, and l in one molecule of the compound represented by formula (1) is an integer from 1 to 200; and in formulae (2) to (4), each * represents a position of bonding.

<12> The polyelectrolyte according to <11>, wherein each of A in formula (1), A in formula (3), and A in formula (4) is P=O.

<13> The polyelectrolyte according to <11> or <12>, wherein each of Z in formula (1), Z in formula (3), and Z in formula (4) is the $OZ^1$ group.

<14> A lithium secondary battery, comprising: a positive electrode; a negative electrode including, as a negative electrode active material, at least one selected from the group consisting of metal lithium, a lithium-containing alloy, a metal or alloy capable of alloying with lithium, an oxide capable of doping and dedoping of lithium ions, a transition metal nitride capable of doping and dedoping of lithium ions, and a carbon material capable of doping and dedoping of lithium ions; and the non-aqueous electrolyte solution for a battery according to any one of <1> to <5> or the polyelectrolyte according to any one of claims <11> to <13>.

<15> A lithium secondary battery, obtained by charging and discharging a lithium secondary battery comprising: a positive electrode; a negative electrode including, as a negative electrode active material, at least one selected from the group consisting of metal lithium, a lithium-containing alloy, a metal or alloy capable of alloying with lithium, an oxide capable of doping and dedoping of lithium ions, a transition metal nitride capable of doping and dedoping of lithium ions, and a carbon material capable of doping and dedoping of lithium ions; and the non-aqueous electrolyte solution for a battery according to any one of <1> to <5> or the polyelectrolyte according to any one of claims <11> to <13>.

Advantages Effects of the Invention

According to the present invention, a non-aqueous electrolyte solution for a battery, a novel compound and a polyelectrolyte that can each improve an initial resistance characteristic of a battery, and a lithium secondary battery with an improved initial resistance characteristic can be provided.

BRIEF DESCRIPTION OF DRAWING

FIG. 1 is a schematic cross sectional view of a coin battery showing an example of the lithium secondary battery of the invention.

DESCRIPTION OF EMBODIMENTS

The non-aqueous electrolyte solution for a battery (hereinafter referred also to merely as the "non-aqueous electrolyte solution") and the polyelectrolyte of the invention each contain at least one kind of a compound represented by the following formula (1).

The non-aqueous electrolyte solution and the polyelectrolyte of the invention are made to have this structural requirement, thereby making it possible to improve an initial resistance characteristic of a battery.

Reasons why this advantageous effect can be obtained are unclear. However, the reasons are presumed as follows: The compound represented by formula (1) has a property of being easily reduced. As a result, a film originating from the compound represented by formula (1) is formed on the surface of the negative electrode. This film makes it possible to restrain a resistance increase. When the battery contains, in particular, a solvent, the compound represented by formula (1) is more easily reduced than the solvent. As a result, the film originating from the compound represented by formula (1) is antecedently formed on the surface of the negative electrode. It is presumed that the film makes it possible to suppress any contact between the negative electrode and the solvent, and the decomposition of the solvent, and thereby the film makes it possible to suppress an increase in the resistance.

In recent years, (particularly about lithium secondary batteries for automobiles), among the battery performances, an increase in output power and an increase in lifespan are required. More specifically, batteries have been required to both minimize resistance of the batteries under various operation conditions and improve the lifespan performance of the batteries.

One of the factors for a resistance increase of a battery is a film formed on the surface of its negative electrode, the film being based on a decomposed product of the solvent, or an inorganic salt therein. On the surface of the negative electrode, metallic lithium is present in negative electrode active material in accordance with conditions for charging the battery; accordingly, it is thought that a reductive decomposition reaction of the electrolyte solution is caused. When such a reductive decomposition reaction is continuously caused, the battery resistance increases and charge-discharge efficiency decreases, thereby being lowered in energy density. Also in the positive electrode, a deterioration reaction is caused with time, and thus the battery resistance continuously increases. As a result, the battery performance may be lowered.

Regarding this point, the non-aqueous electrolyte solution and the polyelectrolyte of the invention can improve also in lifespan performance (storage property) of such a battery. A reason therefor is presumed as follows: The non-aqueous electrolyte solution and the polyelectrolyte of the invention each contain the compound represented by formula (1), thereby restraining the above-mentioned continuous reductive decomposition reaction and deterioration reaction with time.

Hereinafter, the compound represented by formula (1) will be described.

[Compound Represented by Formula (1)]

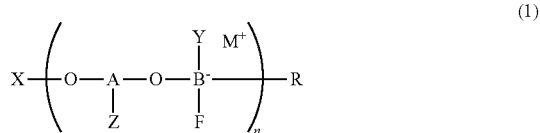

(1)

(2)

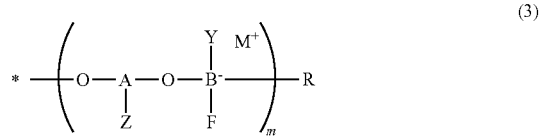

(3)

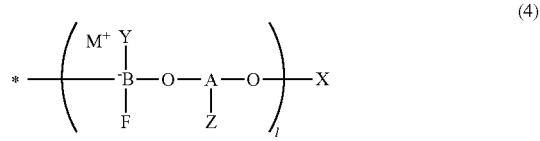

(4)

In formulae (1) to (4), each A represents a phosphorus atom or P=O; each R represents a hydrogen atom, a halogen atom, an alky group, an aryl group, an alkoxy group, or an aryloxy group; each X represents a hydrogen atom, an alkyl group, an aryl group, an alkali metal atom, or a group represented by formula (2); each Y represents a hydrogen atom, a halogen atom, an alkyl group, an aryl group, an alkoxy group, an aryloxy group, or a group represented by formula (3); each Z represents a hydrogen atom, an alkyl group, an aryl group, or an OZ$^1$ group wherein Z$^1$ represents a hydrogen atom, an alkyl group, an aryl group, an alkali metal atom, a group represented by formula (2), or a group represented by formula (4); each M represents an alkali metal atom; n represents an integer of 1 or more, m represents an integer of 1 or more, and l represents an integer of 1 or more, provided that a sum of n, m, and l in one molecule of the compound represented by formula (1) is an integer from 1 to 200; and in formulae (2) to (4), each * represents a position of bonding.

Needless to say, in formulae (1) to (4), B, O, F and P are a boron atom, an oxygen atom, a fluorine atom and a phosphorus atom, respectively.

When the compound represented by formula (1) contains two or more of A, two or more of A may be the same as or different from each other. It is also applicable to R, X, Y, M, Z and $Z^1$.

When n in formula (1) is, for example, two or more, two or more of A may be the same as or different from each other. Furthermore, A in formula (1), A in formula (3), and A in formula (4) may be the same as or different from each other.

When the compound represented by formula (1) contains two or more groups each represented by formula (2), the two or more groups each represented by formula (2) may be the same as or different from each other. It is also applicable to each group in formula represented by formula (3) and each group in formula represented by formula (4).

Specific examples of each "halogen atom" in formulae (1) to (4) include fluorine atom, chlorine atom, bromine atom and iodine atom.

The halogen atom is preferably a fluorine atom.

In formulae (1) to (4), each "alkyl group" denotes a linear or branched alkyl group. Specific examples of the alkyl group include a methyl group, an ethyl group, a propyl group, an isopropyl group, a butyl group, an isobutyl group, a sec-butyl group, a tert-butyl group, a pentyl group, a 2-methylbutyl group, a 1-methylpentyl group, a neopentyl group, a 1-ethylpropyl group, a hexyl group, and a 3,3-dimethylbutyl group.

The number of carbon atoms in the alkyl group is preferably from 1 to 6, more preferably from 1 to 3.

In formulae (1) to (4), each "aryl group" denotes an aryl group that may contain, in the structure thereof, a substituent or heteroatom. The aryl group is preferably an aryl group substituted with a fluorine atom. Specific examples of the aryl group include a 2-fluorophenyl group, a 3-fluorophenyl group, a 4-fluorophenyl group, a 2,3-difluorophenyl group, a 2,4-difluorophenyl group, a 2,5-difluorophenyl group, a 2,6-difluorophenyl group, a 3,4-difluorophenyl group, a 3,5-difluorophenyl group, a 2,3,4-trifluorophenyl group, a 2,3,5-trifluorophenyl group, a 2,3,6-trifluorophenyl group, a 2,4,5-trifluorophenyl group, a 2,4,6-trifluorophenyl group, a 3,4,5-trifluorophenyl group, a 2,3,4,5-tetrafluorophenyl group, a 2,3,4,6-tetrafluorophenyl group, a 2,3,5,6-tetrafluorophenyl group, and a pentafluorophenyl group.

The number of carbon atoms in the aryl group is preferably from 6 to 20, more preferably from 6 to 12.

The aryl group is particularly preferably a phenyl group (preferably, a phenyl group substituted with at least one fluorine atom).

In formulae (1) to (4), each "alkoxy group" denotes a linear or branched alkoxy group. Specific examples of the alkoxy group include a methoxy group, ethoxy group, propoxy group, isopropoxy group, butoxy group, isobutoxy group, sec-butoxy group, tert-butoxy group, pentyloxy group, 2-methylbutoxy group, 1-methylpentyloxy group, neopentyloxy group, 1-ethylpropoxy group, hexyloxy group, and 3,3-dimethylbutoxy group.

The number of carbon atoms in the alkoxy group is preferably from 1 to 6, more preferably from 1 to 3.

The aryl group contained in the structure of each "aryloxy group" in formulae (1) to (4) has the same meaning as the above-mentioned aryl group.

The aryloxy group is preferably an unsubstituted phenoxy group, or a phenoxy group substituted with a fluorine atom. Specific examples of the aryloxy group include a phenoxy group, a 2-fluorophenoxy group, a 3-fluorophenoxy group, a 4-fluorophenoxy group, a 2,3-difluorophenoxy group, a 2,4-difluorophenoxy group, a 2,5-difluorophenoxy group, a 2,6-difluorophenoxy group, a 3,4-difluorophenoxy group, a 3,5-difluorophenoxy group, a 2,3,4-trifluorophenoxy group, a 2,3,5-trifluorophenoxy group, a 2,3,6-trifluorophenoxy group, a 2,4,5-trifluorophenoxy group, a 2,4,6-trifluorophenoxy group, a 3,4,5-trifluorophenoxy group, a 2,3,4,5-tetrafluorophenoxy group, a 2,3,4,6-tetrafluorophenoxy group, a 2,3,5,6-tetrafluorophenoxy group, and a pentafluorophenoxy group.

Examples of each "alkali metal atom" in formulae (1) to (4) include a lithium atom, a sodium atom, and a potassium atom. Of these examples, a lithium atom is particularly preferred.

In formulae (1) to (4), n represents an integer of 1 or more, m represents an integer of 1 or more, and l represents an integer of 1 or more. However, a sum of n, m, and l in one molecule of the compound represented by formula (1) is an integer from 1 to 200. The sum is preferably an integer from 1 to 100.

As described above, n, m, and l are each an integer of 1 or more. However, in one molecule of the compound represented by formula (1), the sum of n, m, and l is not necessarily an integer of 3 or more, and may be 1 or 2. For example, when the compound represented by formula (1) contains, therein, neither any group represented by formula (3) nor any group represented by formula (4) and further n in formula (1) is 1, the sum is 1.

Furthermore, one molecule of the compound represented by formula (1) may contain more than one m. In this case, needless to say, the expression "the sum of n, m, and l in one molecule of the compound represented by formula (1)" denotes the sum of n, plural of m, and l.

Furthermore, one molecule of the compound represented by formula (1) may contain more than one 1. In this case, needless to say, the expression "the sum of n, m, and l in one molecule of the compound represented by formula (1)" denotes the sum of n, m and plural of l.

When one molecule of the compound represented by formula (1) contains one or more groups (each) represented by formula (2), Y in the group represented by formula (2) and, the group being positioned at a terminal of the one molecule, is a hydrogen atom, a halogen atom, an alkyl group, an aryl group, an alkoxy group, or an aryloxy group.

When one molecule of the compound represented by formula (1) contains one or more groups (each) represented by formula (3), Y in the group represented by formula (3), the group being positioned at a terminal of the one molecule, is a hydrogen atom, a halogen atom, an alkyl group, an aryl group, an alkoxy group, or an aryloxy group, and Z in the group represented by formula (3), the group being positioned at the terminal of the one molecule, is a hydrogen atom, or an alkyl group, an aryl group, or an $OZ^1$ group wherein $Z^1$ is a hydrogen atom, an alkyl group, an aryl group, or an alkali metal atom.

When one molecule of the compound represented by formula (1) contains one or more groups (each) represented by formula (4), Y in the group represented by formula (4), the group positioned at a terminal of the one molecule, is a hydrogen atom, a halogen atom, an alkyl group, an aryl group, an alkoxy group, or an aryloxy group, and Z in the group represented by formula (4), the group positioned at the terminal of the one molecule, is a hydrogen atom, or an alkyl group, an aryl group, or an $OZ^1$ group wherein $Z^1$ is a hydrogen atom, an alkyl group, an aryl group, or an alkali metal atom.

In the case of using the compound represented by formula (1) as a component of a non-aqueous electrolyte solution, from the viewpoint of solubility, each of n, m, and l in formulae (1) to (4) is independently an integer, preferably from 1 to 30, more preferably from 1 to 10, still more preferably from 1 to 5.

In the case of using the compound represented by formula (1) as a component of a non-aqueous electrolyte solution, the sum of n, m, and l in one molecule of the compound represented by formula (1) is an integer preferably from 1 to 30, more preferably from 1 to 10, still more preferably from 1 to 5.

In the case of using the compound represented by formula (1) as at least a part of a polyelectrolyte (for example, at least a part of a skeleton that forms a polymeric component of the polyelectrolyte), each of n, m, and l in formulae (1) to (4) is independently an integer, preferably of 5 or more, more preferably of 10 or more. In the case of using the compound represented by formula (1) as at least a part of the polyelectrolyte, the upper limit of each of n, m, and l is appropriately set to adjust the sum of n, m, and l in one molecule of the compound to an integer of 200 or less.

However, the polyelectrolyte may contain not only a compound in which the sum of n, m, and l in one molecule is an integer from 1 to 200, but also a compound in which the sum of n, m, and l in one molecule is more than 200.

In the case of using the compound represented by formula (1) as at least a part of a polyelectrolyte (for example, at least a part of a skeleton that forms a polymeric component of the polyelectrolyte), the sum of n, m, and l in one molecule of the compound represented by formula (1) is an integer preferably of 5 or more, more preferably of 10 or more. In the case of using the compound represented by formula (1) as at least a part of the polyelectrolyte, the upper limit of the sum is an integer of 200. In this case, the sum is preferably an integer of 100 or less.

However, the polyelectrolyte may contain not only a compound in which the sum of n, m, and l in one molecule is an integer from 1 to 200, but also a compound in which the sum of n, m, and l in one molecule is more than 200.

As described above, when n in formulae (1) to (4) is 2 or more, two or more of A may be the same as or different from each other. It is also applicable to Y, Z, $Z^1$, and M.

In formula (1), A is preferably P=O.

More preferably, each of A in formula (1), A in formula (3), and A in formula (4) is P=O.

A compound represented by formula (1), in which A is P=O, is a compound represented by the following formula (5):

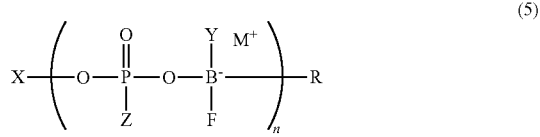

(5)

In formula (5), R, X, Y, Z, M and n have the same meanings and the same preferred scopes or ranges as R, X, Y, Z, M and n in formula (1), respectively.

The following will describe preferred embodiments of the compound represented by formula (1) (including a case of the compound represented by formula (5); the same is applied to the following description).

As described above, A in formula (1) represents a phosphorus atom or P=O, and is particularly preferably P=O.

As described above, R in formula (1) represents a hydrogen atom, a halogen atom, an alky group, an aryl group, an alkoxy group, or an aryloxy group. R is preferably a halogen atom, an alky group, an aryl group, alkoxy group, or an aryloxy group, more preferably a halogen atom or an alkoxy group.

As described above, X in formula (1) represents a hydrogen atom, an alkyl group, an aryl group, an alkali metal atom, or a group represented by formula (2). X is preferably an alkali metal atom, or a group represented by formula (2).

As described above, Y in formula (1) represents a hydrogen atom, a halogen atom, an alkyl group, an aryl group, an alkoxy group, an aryloxy group, or a group represented by formula (3). Y is preferably a hydrogen atom, a halogen atom, an alkyl group, an aryl group, an alkoxy group, or an aryloxy group, more preferably a halogen atom, an alkyl group, an aryl group, an alkoxy group, or an aryloxy group, particularly preferably a halogen atom or an alkoxy group.

As described above, Z in formula (1) represents a hydrogen atom, or an alkyl group, an aryl group, or an $OZ^1$ group. Z is preferably an alkyl group, an aryl group, or an $OZ^1$ group, more preferably an $OZ^1$ group.

As described above, $Z^1$ in formula (1) represents a hydrogen atom, an alkyl group, an aryl group, an alkali metal atom, a group represented by formula (2) or a group represented by formula (4). $Z^1$ is preferably a hydrogen atom, an alkyl group, an aryl group, an alkali metal atom, or a group represented by formula (2), preferably an alkali metal atom, or a group represented by formula (2).

As described above, M in formula (1) represents an alkali metal atom. M is preferably a lithium atom, a sodium atom or a potassium atom, particularly preferably a lithium atom.

As described above, n in formula (1) represents an integer of 1 or more. Specifically, n is an integer from 1 to 200, preferably an integer from 1 to 100, more preferably an integer from 1 to 30, still more preferably an integer from 1 to 10, particularly preferably an integer from 1 to 5.

The following will describe preferred embodiments of the group represented by formula (2).

As described above, R in formula (2) represents a hydrogen atom, a halogen atom, an alky group, an aryl group, an alkoxy group, or an aryloxy group. R is preferably a halogen atom, an alky group, an aryl group, an alkoxy group, or an aryloxy group, more preferably a halogen atom or an alkoxy group.

As described above, Y in formula (2) represents a hydrogen atom, a halogen atom, an alkyl group, an aryl group, an alkoxy group, aryloxy group, or a group represented by formula (3). Y is preferably a hydrogen atom, a halogen atom, an alkyl group, an aryl group, an alkoxy group, or aryloxy group, more preferably a halogen atom, an alkyl group, an aryl group, an alkoxy group, or an aryloxy group, particularly preferably a halogen atom or an alkoxy group.

As described above, M in formula (2) represents an alkali metal atom. M is preferably a lithium atom, a sodium atom or a potassium atom, particularly preferably a lithium atom.

The following will describe preferred embodiments of the group represented by formula (3).

As described above, A in formula (3) represents a phosphorus atom or P=O, and is particularly preferably P=O.

As described above, R in formula (3) represents a hydrogen atom, a halogen atom, an alky group, an aryl group, an alkoxy group, or an aryloxy group. R is preferably a halogen atom, an alkyl group, an aryl group, an alkoxy group, or an aryloxy group, more preferably a halogen atom or an alkoxy group.

As described above, Y in formula (3) represents a hydrogen atom, a halogen atom, an alkyl group, an aryl group, an alkoxy group, an aryloxy group, or a group represented by formula (3). Y is preferably a hydrogen atom, a halogen atom, an alkyl group, an aryl group, an alkoxy group, or an aryloxy group, more preferably a halogen atom, an alkyl group, an aryl group, an alkoxy group, or an aryloxy group, particularly preferably a halogen atom or an alkoxy group.

As described above, Z in formula (3) represents a hydrogen atom, or an alkyl group, an aryl group, or an $OZ^1$ group. Z is preferably an alkyl group, an aryl group, or an $OZ^1$ group, more preferably an $OZ^1$ group.

As described above, $Z^1$ in formula (3) represents a hydrogen atom, an alkyl group, an aryl group, an alkali metal atom, a group represented by formula (2), or a group represented by formula (4). $Z^1$ is preferably a hydrogen atom, an alkyl group, an aryl group, an alkali metal atom, or a group represented by formula (2), preferably an alkali metal atom, or a group represented by formula (2).

As described above, M in formula (3) represents an alkali metal atom. M is preferably a lithium atom, a sodium atom or a potassium atom, particularly preferably a lithium atom.

As described above, m in formula (3) represents an integer of 1 or more. m is preferably an integer from 1 to 199, more preferably an integer from 1 to 100, still more preferably an integer from 1 to 30, even more preferably an integer from 1 to 10, and particularly preferably an integer from 1 to 5.

The following will describe preferred embodiments of the group represented by formula (4).

As described above, A in formula (4) represents a phosphorus atom or P=O, and is particularly preferably P=O.

As described above, X in formula (4) represents a hydrogen atom, an alkyl group, an aryl group, an alkali metal atom, or a group represented by formula (2). X is preferably an alkali metal atom, or a group represented by formula (2).

As described above, Yin formula (4) represents a hydrogen atom, a halogen atom, an alkyl group, an aryl group, an alkoxy group, an aryloxy group, or a group represented by formula (3). Y is preferably a hydrogen atom, a halogen atom, an alkyl group, an aryl group, an alkoxy group, or an aryloxy group, more preferably a halogen atom, an alkyl group, an aryl group, an alkoxy group, or an aryloxy group, particularly preferably a halogen atom or an alkoxy group.

As described above, Z in formula (4) represents a hydrogen atom, or an alkyl group, an aryl group, or an $OZ^1$ group. Z is preferably an alkyl group, an aryl group, or an $OZ^1$ group, more preferably an $OZ^1$ group.

In the compound represented by formula (1), each of Z in formula (1), Z in formula (3), and Z in formula (4) is particularly preferably an $OZ^1$ group.

As described above, $Z^1$ in formula (4) represents a hydrogen atom, an alkyl group, an aryl group, an alkali metal atom, a group represented by formula (2), or a group represented by formula (4). $Z^1$ is preferably a hydrogen atom, an alkyl group, an aryl group, an alkali metal atom, or a group represented by formula (2), preferably an alkali metal atom, or a group represented by formula (2).

As described above, M in formula (4) represents an alkali metal atom. M is preferably a lithium atom, a sodium atom or a potassium atom, particularly preferably a lithium atom.

As described above, l in formula (4) represents an integer of 1 or more. l is preferably an integer from 1 to 199, more preferably an integer from 1 to 100, still more preferably an integer from 1 to 30, even more preferably an integer from 1 to 10, particularly preferably an integer from 1 to 5.

Examples of a particularly preferable embodiment of the compound represented by formula (1) are embodiments in which n in formula (1) is an integer from 1 to 30 (preferably an integer from 1 to 10), each of Y in formula (1) and Yin formula (2) is independently a hydrogen atom, a halogen atom, an alkyl group, an aryl group, an alkoxy group, or an aryloxy group, Z in formula (1) is a hydrogen atom, or an alkyl group, an aryl group, or an $OZ^1$ group wherein $Z^1$ is a hydrogen atom, an alkyl group, an aryl group, an alkali metal atom, or a group represented by formula (2). Of these embodiments, an embodiment in which Z in formula (1) is an $OZ^1$ group is more preferred.

Furthermore, one molecule of the compound represented by formula (1) contains a structural unit represented by the following formula (1A).

In the structure of the whole of the compound represented by formula (1), the structural unit represented by formula (1A) is important for producing the advantageous effect (an improvement of a battery in initial resistance characteristic) of the invention.

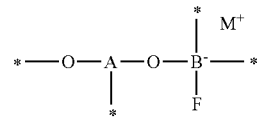

(1A)

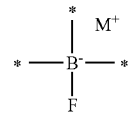

(2A)

In formula (1A), * represents a position of bonding.

In formula (1A), A and M have the same meanings and preferred scopes as A and M in formula (1), respectively.

The atom O positioned at a terminal of formula (1A) is bonded to a hydrogen atom, an alkyl group, an aryl group, an alkali metal atom, or a group represented by formula (2A). However, when two or more structural units each represented by formula (1A) are contained in (one molecule of) the compound represented by formula (1), O in a specified structural unit of the structural units each represented by formula (1A) may be bonded to B in a different structural unit of the structural units each represented by formula (1A).

In formula (2A), * represents a position of bonding.

In formula (2A), M has the same meaning and preferred scope as M in formula (1).

In formula (2A), B is bonded to a structural unit represented by formula (1A), a hydrogen atom, a halogen atom, an alkyl group, an aryl group, an alkoxy group, or an aryloxy group.

When the compound represented by formula (1) contains, therein, two or more structural units each represented by formula (1A), B in formula (2A) may be bonded to the two or more structural units each represented by formula (1A).

As described above, the sum of n, m, and l in one molecule of the compound represented by formula (1) is an integer from 1 to 200. Namely, the number of structural units each represented by formula (1A) (hereinafter referred to also as a "structural unit (1A)") and contained in the compound represented by formula (1) is from 1 to 200.

In the compound represented by formula (1), the structural units (1A) may be linked to each other (in the form of, for example, a network) to have a crosslinked structure having plural branches.

The number of the structural units (1A) contained in the compound represented by formula (1) ranges preferably from 1 to 100, more preferably from 1 to 30, still more preferably from 1 to 10, particularly preferably from 1 to 5.

When the compound represented by formula (1) contains therein two or more structural units (1A), two or more of A may be the same as or different from each other. In the same manner, in this case, two or more Ms may be the same as or different from each other.

In the case of using the compound represented by formula (1) as a component of a non-aqueous electrolyte solution, the number of the structural units (1A) contained in the compound represented by formula (1) ranges preferably from 1 to 30, more preferably from 1 to 10, particularly preferably from 1 to 5.

In the case of using the compound represented by formula (1) as at least a part of a polyelectrolyte (for example, at least a part of a skeleton that forms a polymeric component of the polyelectrolyte), the number of the structural units (1A) contained in the compound represented by formula (1) is preferably 5 or more, more preferably 10 or more.

In this case also, the upper limit of the number of the structural units (1A) contained in the compound represented by formula (1) is 200. The number of the structural units (1A) is preferably 100 or less.

However, the polyelectrolyte may contain not only the compound represented by formula (1) in which the number of the structural units (1A) is an integer from 1 to 200, but also a compound in which the number of the structural units (1A) is more than 200.

The molecular weight of the compound represented by formula (1) is preferably from 100 to 100000, more preferably from 100 to 10000, particularly preferably from 100 to 5000.

The molecular weight herein denotes the weight-average molecular weight.

The following will demonstrate specific examples (examples 1 to 33) of the compound represented by formula (1). However, the invention is not limited by these examples.

In these specific examples, "$C_6H_5$" represents a phenyl group, and "$C_6F_5$" represents a perfluorophenyl group.

(example 1)

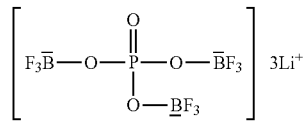

(example 2)

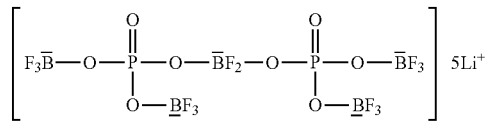

(example 3)

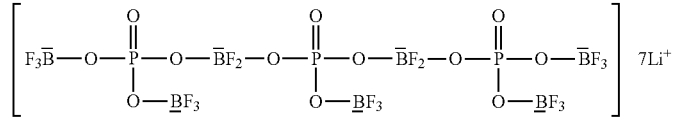

(example 4)

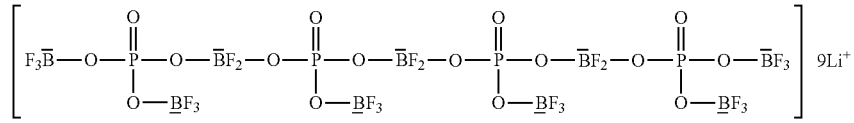

(example 5)

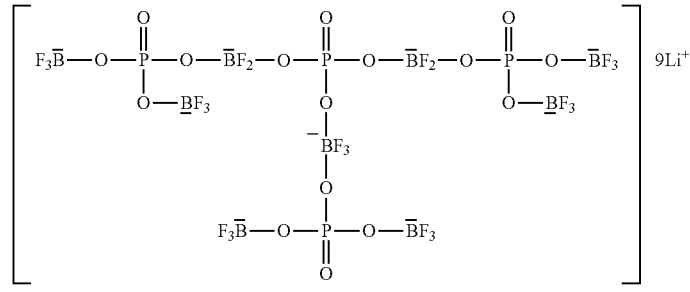

(example 6)

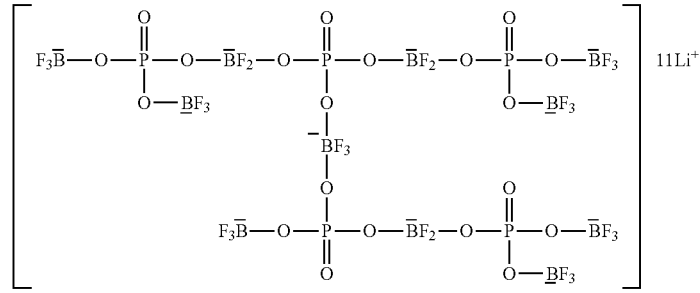

-continued
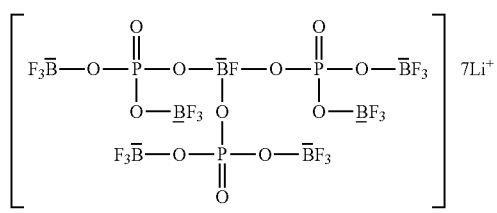
(example 7)
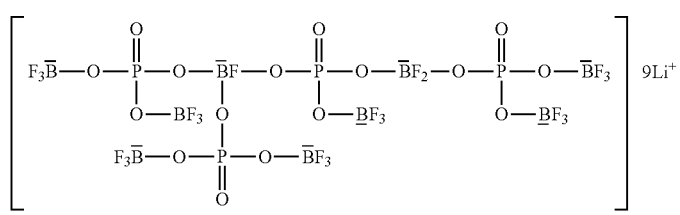
(example 8)
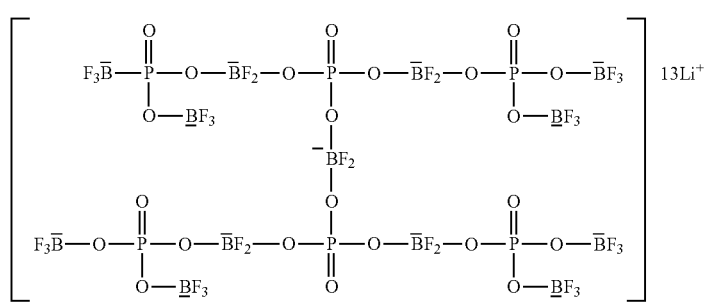
(example 9)
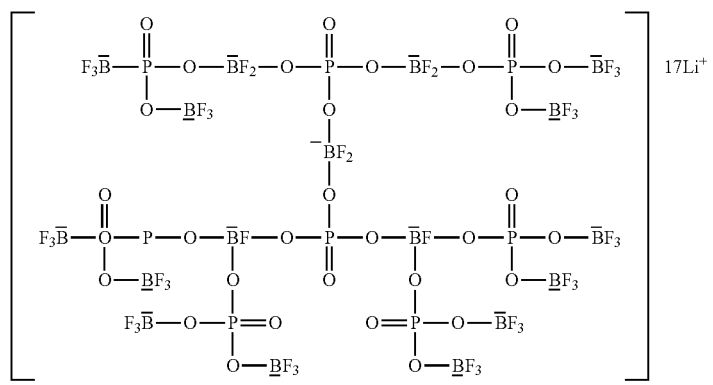
(example 10)
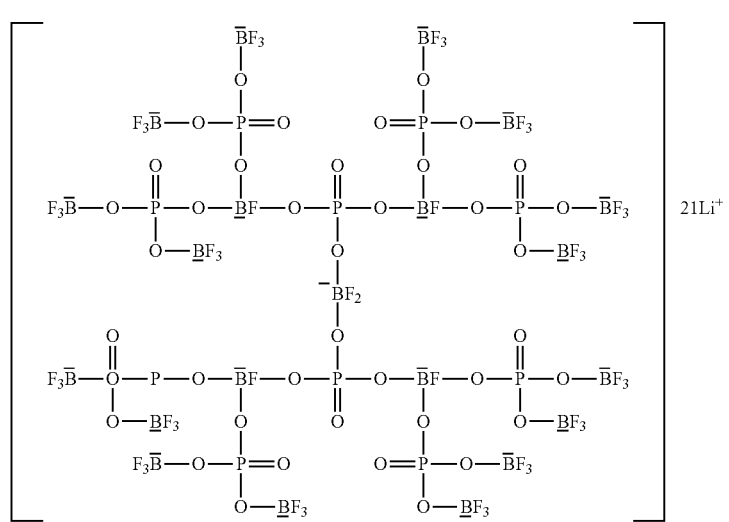
(example 11)

(example 12)
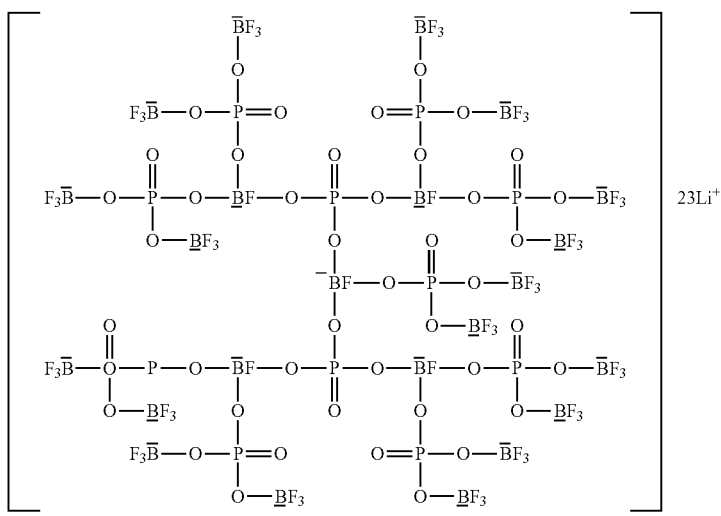
(example 13)
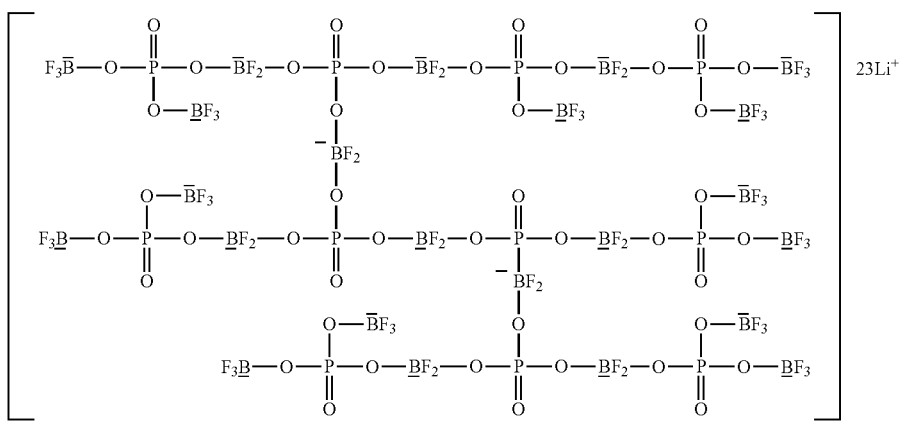
(example 14)
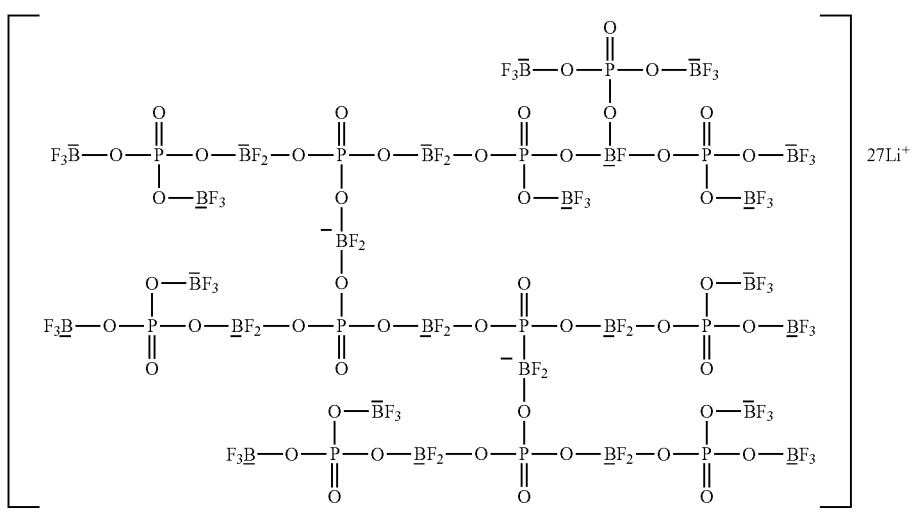
(example 15)
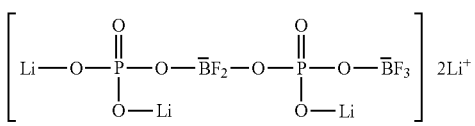
(example 16)
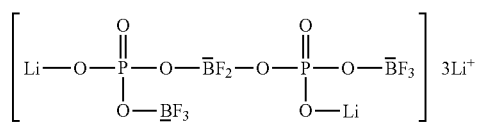

-continued
(example 17)
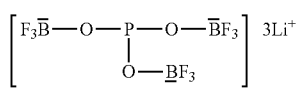
(example 18)
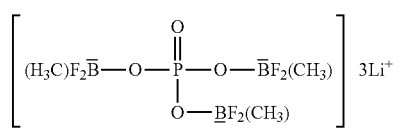
(example 19)
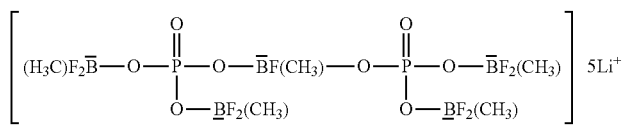
(example 20)
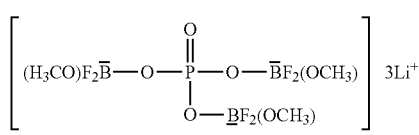
(example 21)
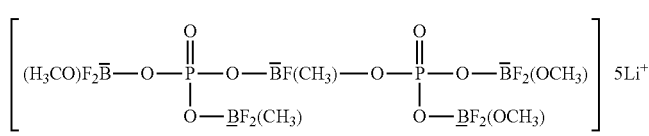
(example 22)
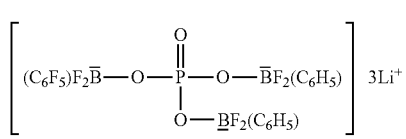
(example 23)
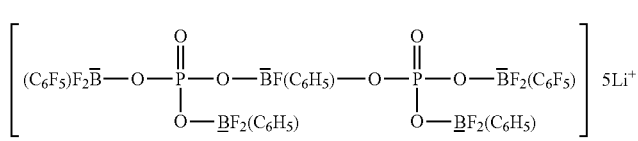
(example 24)
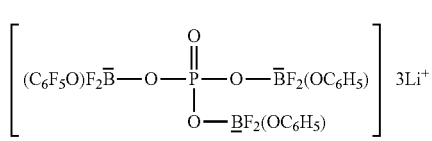
(example 25)
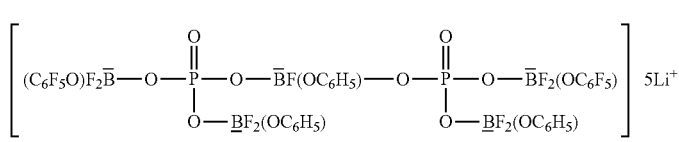
(example 26)
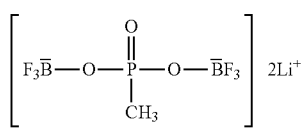
(example 27)
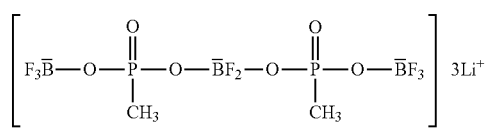
(example 28)
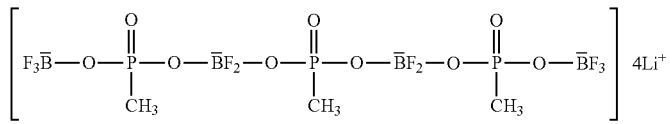
(example 29)
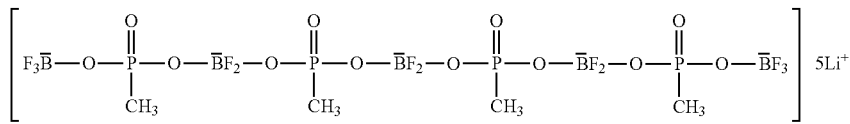

(example 30)

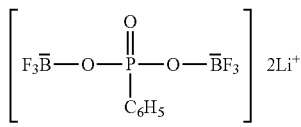

(example 31)

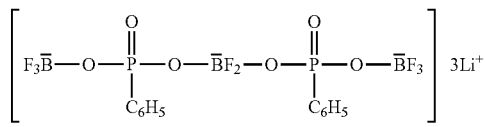

(example 32)

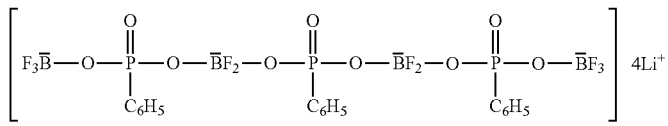

(example 33)

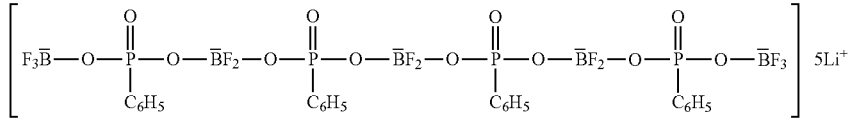

The method for synthesizing the compound represented by formula (1) is not particularly limited. The compound represented by formula (1) may be synthesized, for example, by causing at least one selected from the group consisting of alkali metal salts of a phosphoric acid, alkali metal salts of a phosphorous acid, alkali metal salts of a phosphonic acid, alkali metal salts of an alkylphosphonic acid, and alkali metal salts of an arylphosphonic acid to react with at least one selected from the group consisting of boron compounds each containing at least one bond between a fluorine atom and a boron atom (preferably, boron trifluoride) (as needed, further with at least one selected from the group consisting of an alkali metal fluoride (preferably, lithium fluoride)).

Hereinafter, alkali metal salts of phosphoric acid, alkali metal salts of phosphorous acid, alkali metal salts of phosphonic acid, alkali metal salts of alkylphosphonic acid, and alkali metal salts of arylphosphonic acid may be collectively referred to merely as a "phosphorus compound".

[Non-aqueous Electrolyte Solution]

The non-aqueous electrolyte solution of the invention contains at least one kind of a compound represented by the above-mentioned formula (1).

The content of the compound represented by formula (1) (if two or more kinds are used, the total content) in the non-aqueous electrolyte solution of the invention is, with respect to the total mass of the non-aqueous electrolyte solution, preferably from 0.01% by mass to 10% by mass, more preferably from 0.05% by mass to 5% by mass, and particularly preferably from 0.1% by mass to 2% by mass.

The other components of the non-aqueous electrolyte solution are described below.

The non-aqueous electrolyte solution commonly contains an electrolyte and a non-aqueous solvent.

<Non-aqueous Solvent>

Regarding the non-aqueous solvent related to the invention, various known solvents can be appropriately selected, but it is preferable to use a cyclic aprotic solvent and/or a linear aprotic solvent.

When an increase in the flash point of the solvent is intended to enhance the safety of the battery, it is preferable to use a cyclic aprotic solvent as the non-aqueous solvent.

(Cyclic Aprotic Solvent)Yuudennritu

Examples of the cyclic aprotic solvent that can be used include a cyclic carbonate, a cyclic carboxylic acid ester, a cyclic sulfone, and a cyclic ether.

The cyclic aprotic solvent may be used alone, or a mixture of plural kinds may also be used.

The mixing proportion of the cyclic aprotic solvent in the non-aqueous solvent is preferably from 10% by mass to 100% by mass, even more preferably from 20% by mass to 90% by mass, and particularly preferably from 30% by mass to 80% by mass. When such a ratio is employed, the conductivity of the electrolyte solution that is related to the charge-discharge characteristics of the battery can be increased.

Specific examples of the cyclic carbonate include ethylene carbonate, propylene carbonate, 1,2-butylene carbonate, 2,3-butylene carbonate, 1,2-pentylene carbonate, and 2,3-pentylene carbonate. Among these, ethylene carbonate and propylene carbonate having high dielectric constants are suitably used. In the case of a battery using graphite as the negative electrode active material, ethylene carbonate is more preferable. Also, two or more kinds of these cyclic carbonates may also be used in mixture.

Specific examples of the cyclic carboxylic acid ester include γ-butyrolactone, δ-valerolactone, and alkyl-substituted forms such as methyl-γ-butyrolactone, ethyl-γ-butyrolactone, and ethyl-δ-valerolactone.

A cyclic carboxylic acid ester has a low vapor pressure, has low viscosity, has a high dielectric constant, and can lower the viscosity of the electrolyte solution without decreasing the flash point of the electrolyte solution and the degree of dissociation of the electrolyte. For this reason, a cyclic carboxylic acid ester has a feature that the conductivity of the electrolyte solution, which is an index associated with the discharge characteristics of a battery, can be increased without increasing the inflammability of the electrolyte solution. Therefore, in the case where an improvement in the flash point of the solvent is intended, it is preferable to use a cyclic carboxylic acid ester as the cyclic aprotic solvent. Among cyclic carboxylic acid esters, γ-butyrolactone is most preferred.

Furthermore, it is preferable to use a cyclic carboxylic acid ester as a mixture with another cyclic aprotic solvent. For example, a mixture of a cyclic carboxylic acid ester and a cyclic carbonate and/or an acyclic carbonate may be used.

Examples of the cyclic sulfone include sulfolane, 2-methylsulfolane, 3-methylsulfolane, dimethylsulfone, diethylsulfone, dipropylsulfone, methylethylsulfone, and methylpropylsulfone.

Examples of the cyclic ether include dioxolane.

(Acyclic Aprotic Solvent)

Examples of the acyclic aprotic solvent in the invention that can be used include an acyclic carbonate, an acyclic carboxylic acid ester, an acyclic ether, and an acyclic phosphoric acid ester.

The mixing proportion of the acyclic aprotic solvent in the non-aqueous solvent may be from 10% by mass to 100% by mass, more preferably from 20% by mass to 90% by mass, and particularly preferably from 30% by mass to 80% by mass.

Specific examples of the acyclic carbonate include dimethyl carbonate, methyl ethyl carbonate, diethyl carbonate, methyl propyl carbonate, methyl isopropyl carbonate, ethyl propyl carbonate, dipropyl carbonate, methyl butyl carbonate, ethyl butyl carbonate, dibutyl carbonate, methyl pentyl carbonate, ethyl pentyl carbonate, dipentyl carbonate, methyl heptyl carbonate, ethyl heptyl carbonate, diheptyl carbonate, methyl hexyl carbonate, ethyl hexyl carbonate, dihexyl carbonate, methyl octyl carbonate, ethyl octyl carbonate, dioctyl carbonate, and methyl trifluoroethyl carbonate. These acyclic carbonates may also be used as mixtures of two or more kinds.

Specific examples of the acyclic carboxylic acid ester include methyl pivalate.

Specific examples of the acyclic ether include dimethoxyethane.

Specific examples of the acyclic phosphoric acid ester include trimethyl phosphate.

(Combination of Solvents)

The non-aqueous solvent used in the non-aqueous electrolyte solution related to the invention may be used singly or as a mixture of plural kinds. Furthermore, only cyclic aprotic solvents may be used singly or as a combination of plural kinds; only acyclic aprotic solvents may be used singly or as a combination of plural kinds; or mixtures of cyclic aprotic solvents and acyclic protic solvents may also be used. Particularly when an enhancement of the rate characteristics and the low temperature characteristics of the battery is intended, it is preferable to use a cyclic aprotic solvent and an acyclic aprotic solvent in combination as the non-aqueous solvent.

Furthermore, in view of the electrochemical stability of the electrolyte solution, it is most preferable to apply a cyclic carbonate as the cyclic aprotic solvent, and to apply an acyclic carbonate as the acyclic aprotic solvent. Furthermore, when a combination of a cyclic carboxylic acid ester and a cyclic carbonate and/or acyclic carbonate is used, the conductivity of the electrolyte solution related to the charge-discharge characteristics of the battery can be increased.

Specific examples of the combination of a cyclic carbonate and an acyclic carbonate include ethylene carbonate with dimethyl carbonate; ethylene carbonate with methyl ethyl carbonate; ethylene carbonate with diethyl carbonate; propylene carbonate with dimethyl carbonate; propylene carbonate with methyl ethyl carbonate; propylene carbonate with diethyl carbonate; ethylene carbonate with propylene carbonate and methyl ethyl carbonate; ethylene carbonate with propylene carbonate and diethyl carbonate; ethylene carbonate with dimethyl carbonate and methyl ethyl carbonate; ethylene carbonate with dimethyl carbonate and diethyl carbonate; ethylene carbonate with methyl ethyl carbonate and diethyl carbonate; ethylene carbonate with dimethyl carbonate, methyl ethyl carbonate and diethyl carbonate; ethylene carbonate with propylene carbonate, dimethyl carbonate and methyl ethyl carbonate; ethylene carbonate with propylene carbonate, dimethyl carbonate and diethyl carbonate; ethylene carbonate with propylene carbonate, methyl ethyl carbonate and diethyl carbonate; and ethylene carbonate with propylene carbonate, dimethyl carbonate, methyl ethyl carbonate and diethyl carbonate.

The mixing proportion of the cyclic carbonate and the acyclic carbonate is such that when expressed as a mass ratio, the ratio of cyclic carbonate:acyclic carbonate is preferably 5:95 to 80:20, more preferably 10:90 to 70:30, and particularly preferably 15:85 to 55:45. When such ratios are employed, an increase in the viscosity of the electrolyte solution is suppressed, and the degree of dissociation of the electrolyte can be increased. Therefore, the conductivity of the electrolyte solution related to the charge-discharge characteristics of a battery can be increased. Furthermore, the solubility of the electrolyte can be further increased. Accordingly, since an electrolyte solution having excellent electrical conductivity at normal temperature or at a low temperature can be obtained, the rate characteristics of a battery at normal temperature to a low temperature can be improved.

Specific examples of the combination of a cyclic carboxylic acid ester with a cyclic carbonate and/or an acyclic carbonate include γ-butyrolactone with ethylene carbonate; γ-butyrolactone with ethylene carbonate and dimethyl carbonate; γ-butyrolactone with ethylene carbonate and methyl ethyl carbonate; γ-butyrolactone with ethylene carbonate and diethyl carbonate; γ-butyrolactone with propylene carbonate; γ-butyrolactone with propylene carbonate and dimethyl carbonate; γ-butyrolactone with propylene carbonate and methyl ethyl carbonate; γ-butyrolactone with propylene carbonate and diethyl carbonate; γ-butyrolactone with ethylene carbonate and propylene carbonate; γ-butyrolactone with ethylene carbonate, propylene carbonate and dimethyl carbonate; γ-butyrolactone with ethylene carbonate, propylene carbonate and methyl ethyl carbonate; γ-butyrolactone with ethylene carbonate, propylene carbonate and diethyl carbonate; γ-butyrolactone with ethylene carbonate, dimethyl carbonate and methyl ethyl carbonate; γ-butyrolactone with ethylene carbonate, dimethyl carbonate and diethyl carbonate; γ-butyrolactone with ethylene carbonate, methyl ethyl carbonate and diethyl carbonate; γ-butyrolactone with ethylene carbonate, dimethyl carbonate, methyl ethyl carbonate, and diethyl carbonate; γ-butyrolactone with ethylene carbonate, propylene carbonate, dimethyl carbonate and methyl ethyl carbonate; γ-butyrolactone with ethylene carbonate, propylene carbonate, dimethyl carbonate and diethyl carbonate; γ-butyrolactone with ethylene carbonate, propylene carbonate, methyl ethyl carbonate, and diethyl carbonate; γ-butyrolactone with ethylene carbonate, propylene carbonate, dimethyl carbonate, methyl ethyl carbonate, and diethyl carbonate; γ-butyrolactone with sulfolane; γ-butyrolactone with ethylene carbonate and sulfolane; γ-butyrolactone with propylene carbonate and sulfolane; γ-butyrolactone with ethylene carbonate, propylene carbonate and sulfolane; and γ-butyrolactone with sulfolane and dimethyl carbonate.

(Other Solvents)

The non-aqueous electrolyte solution related to the invention may also include other solvent in addition to the solvents described above, as the non-aqueous solvent. Specific examples of the other solvent include amides such as dimethylformamide; acyclic carbamates such as methyl-N, N-dimethyl carbamate; cyclic amides such as N-methylpyrrolidone; cyclic ureas such as N,N-dimethylimidazolidinone; boron compounds such as trimethyl borate, triethyl borate, tributyl borate, trioctyl borate, and trimethylsilyl borate; and polyethylene glycol derivatives represented by the following formulas:

$$HO(CH_2CH_2O)_aH$$

$$HO[CH_2CH(CH_3)O]_bH$$

$$CH_3O(CH_2CH_2O)_cH$$

$$CH_3O[CH_2CH(CH_3)O]_dH$$

$$CH_3O(CH_2CH_2O)_eCH_3$$

$$CH_3O[CH_2CH(CH_3)O]_fCH_3$$

$$C_9H_{19}PhO(CH_2CH_2O)_g[CH(CH_3)O]_hCH_3$$

(Ph represents a phenyl group)

$$CH_3O[CH_2CH(CH_3)O]_iCO[OCH(CH_3)CH_2]_jOCH_3$$

In the above formulas, a to f each represent an integer from 5 to 250; g to j each represent an integer from 2 to 249; $5 \leq g+h \leq 250$; and $5 \leq i+j \leq 250$.

[Electrolyte]

The non-aqueous electrolyte solution of the invention may include various known electrolytes, as long as they are normally used as electrolytes for a non-aqueous electrolyte solution.

Specific examples of the electrolyte in the non-aqueous electrolyte solution of the present invention include tetraalkyl ammonium salts such as $(C_2H_5)_4NPF_6$, $(C_2H_5)_4NBF_4$, $(C_2H_5)_4NClO_4$, $(C_2H_5)_4NAsF_6$, $(C_2H_5)_4N_2SiF_6$, $(C_2H_5)_4NOSO_2C_kF_{(2k+1)}$ (k is an integer from 1 to 8), $(C_2H_5)_4NPF_n[C_kF_{(2k+1)}]_{(6-n)}$ (n is an integer from 1 to 5, and k is an integer from 1 to 8); and lithium salts such as $LiPF_6$, $LiBF_4$, $LiClO_4$, $LiAsF_6$, $Li_2SiF_6$, $LiOSO_2C_kF_{(2k+1)}$ (k is an integer from 1 to 8), and $LiPF_n[C_kF_{(2k+1)}]_{(6-n)}$ (n is an integer from 1 to 5, k is an integer from 1 to 8). In addition, the lithium salt represented by the following formula may also be used.

$LiC(SO_2R^{27})(SO_2R^{28})(SO_2R^{29})$, $LiN(SO_2OR^{30})(SO_2OR^{31})$, $LiN(SO_2R^{32})(SO_2R^{33})$ (wherein $R^{27}$ to $R^{33}$ may be identical or different, and are perfluoroalkyl groups having 1 to 8 carbon atoms). These electrolytes may be used singly, or two or more kinds may be used as mixtures.

Among them, lithium salts are particularly preferred, and $LiPF_6$, $LiBF_4$, $LiOSO_2C_kF_{(2k+1)}$ (k is an integer from 1 to 8), $LiClO_4$, $LiAsF_6$, $LiNSO_2[C_kF_{(2k+1)}]_2$ (k is an integer from 1 to 8), and $LiPF_n[C_kF_{(2k+1)}]_{(6-n)}$ (n is an integer from 1 to 5, and k is an integer from 1 to 8) are even more preferred.

In the invention, the normal concentration of the electrolyte in the non-aqueous electrolyte is preferably from 0.1 mol/L to 3 mol/L, and more preferably from 0.5 mol/L to 2 mol/L.

In the case of using a cyclic carboxylic ester, such as γ-butyrolactone, together as the non-aqueous solvent in the non-aqueous electrolyte solution of the invention, this solution particularly desirably contains $LiPF_6$. Since $LiPF_6$ has a high degree of dissociation, it increases the conductivity of the electrolyte solution, and inhibits the reduction decomposition reaction of the electrolyte solution on the negative electrode. $LiPF_6$ may be used alone, or in combination with other electrolyte. The other electrolyte may be any one as long as it is normally used as an electrolyte for a non-aqueous electrolyte solution, but is preferably a lithium salt other than $LiPF_6$ included in the above-described specific examples of the lithium salt.

Specific examples include: $LiPF_6$ and $LiBF_4$; $LiPF_6$ and $LiN[SO_2C_kF_{(2k+1)}]_2$ (k is an integer from 1 to 8); and $LiPF_6$, $LiBF_4$, and $LiN[SO_2C_kF_{(2k+1)}]$ (k is an integer from 1 to 8).

The proportion of the $LiPF_6$ in the lithium salt is preferably from 1% by mass to 100% by mass, more preferably from 10% by mass to 100% by mass, and even more preferably from 50% by mass to 100% by mass. The concentration of the electrolyte in the non-aqueous electrolyte solution is preferably from 0.1 mol/L to 3 mol/L, and more preferably from 0.5 mol/L to 2 mol/L.

The non-aqueous electrolyte solution according to the invention may contain, as an additive, at least one compound different from the compound represented by formula (1) as long as the object of the invention is not hindered.

Specific examples of the different compound include carbonic esters each having a carbon-carbon unsaturated bond, such as vinylene carbonate, dimethylvinylene carbonate, and divinyl carbonate; carbonic esters each having a fluorine group, such as fluoroethylene carbonate, difluoroethylene carbonate, and methyl-2,2,2-trifluoroethyl carbonate; sultones such as 1,3-propane sultone, 1,4-butane sultone, 1,3-prop-1-ene sultone, 1-methyl-1,3-prop-1-ene sultone, 2-methyl-1,3-prop-1-ene sultone, and 3-methyl-1,3-prop-1-ene sultone; sulfates such as dimethyl sulfate, diethyl sulfate, ethylene sulfate, propylene sulfate, butene sulfate, pentene sulfate, and vinylene sulfate; and sulfur-containing compounds such as sulfolane, 3-sulfolene, and divinylsulfone.

These compounds may be used singly or in combination of two or more thereof.

Of these examples, the following are preferred: vinylene carbonate, fluoroethylene carbonate, 1,3-prop-1-ene sultone, ethylene sulfate, propylene sulfate, butene sulfonate, and pentene sulfate.

The non-aqueous electrolyte solution of the invention is suitable as a non-aqueous electrolyte solution for lithium secondary batteries, and is usable as a non-aqueous electrolyte solution for primary batteries, a non-aqueous electrolyte solution for electrochemical capacitors, or an electrolyte solution for electric double layer capacitors or aluminum electrolyte capacitors.

[Polyelectrolyte]

The polyelectrolyte of the invention contains at least one kind of the compound represented by formula (1).

The form of the polyelectrolyte of the invention is not particularly limited, and may be in the form of a gel-type polyelectrolyte containing a solid polymeric compound and a non-aqueous electrolyte solution (preferably, a gel-type polyelectrolyte in which a solid polymeric compound is impregnated with a non-aqueous electrolyte solution), or in the form of a full-solid polyelectrolyte, which is made only of a solid polymeric compound.

Of these forms, a gel-type polyelectrolyte is preferred since the electrolyte is high in ion conductivity.

In any one of these forms, it is sufficient for the compound represented by formula (1) to be contained in any portion of the polyelectrolyte of the invention.

When the polyelectrolyte of the invention is, for example, in the form of a gel-type polyelectrolyte, the compound represented by formula (1) may be contained in at least a part of the solid polymeric compound (for example, at least a part of a polymeric skeleton of the solid polyelectrolyte), or may be contained in the non-aqueous electrolyte solution as one of the components of the gel-type polyelectrolyte.

In a case where in the gel-type polyelectrolyte, the compound represented by formula (1) is contained in at least a part of the solid polymeric compound, the non-aqueous electrolyte solution, as one of the components of the gel-type polyelectrolyte, may be the non-aqueous electrolyte solution of the invention, or an ordinary non-aqueous electrolyte solution other than the non-aqueous electrolyte solution of the invention.

In a case where the gel-type polyelectrolyte the compound represented by formula (1) is contained in the non-aqueous electrolyte solution as one of the components of the gel-type polyelectrolyte, it is allowable to use, as its solid polymeric compound, an ordinary polyelectrolyte (for example, a polyelectrolyte usable as a separator that will be described later) without especial restriction.

The gel-type polyelectrolyte can be produced by, for example, a method of subjecting a non-aqueous electrolyte solution containing the compound represented by formula (1) to heating treatment, thereby gelatinizing the electrolyte solution.

In this gelatinizing method, it is believed that the compound represented by formula (1) is condensed in the non-aqueous electrolyte solution by the heating treatment to generate a polymeric compound (that is, the polyelectrolyte; the same is applied to the following description) as a condensate of the compound represented by formula (1). It is thought that the generation of the polymeric compound can be confirmed by the gelatinization of the non-aqueous electrolyte solution.

In the gelatinizing method, the temperature for the heating treatment may be 40° C. or higher, or may be from 40° C. to 80° C., and is preferably from 50° C. to 70° C.

In the gelatinizing method, the time for the heating treatment is 1 hour or longer, preferably from 1 hour to 10 hours, more preferably from 2 hours to 5 hours.

In the gelatinizing method, at the time of synthesizing the compound represented by formula (1), the numerical value of the sum of n, m, and 1 is adjustable by selecting the following ratio appropriately from the range of 10/1 to 1/10: the quantity ratio of the above-mentioned phosphorus compound to the above-mentioned boron compound, which contains at least one bond between fluorine and boron atoms.

In the generation of the polymeric compound, X or Z in a specified molecule of the compound represented by formula (1) reacts with R or Y in another molecule of the compound represented by formula (1), and this reaction is repeated, whereby a polymerization of the compound advances. For example, in two molecules of one (example 1) of the specific examples of the compound represented by formula (1), a reaction between X in one of the molecules and R in the other molecule advances to produce one molecule of one (example 2) of the specific examples and one molecule of $LiBF_4$. A reaction between Z in one (example 1) of the specific examples and Y in one (example 2) of the specific examples advances to produce one molecule of one (example 7) of the specific examples and one molecule of $LiBF_4$. In the above-mentioned gelatinizing method, it is believed that by the repetition of such reactions, a polymeric compound is yielded.

A full-solid polyelectrolyte can be produced by attaining, in the gelatinizing method, at least one of an extension of the heating treatment time, and a raise in the heating treatment temperature to remove the non-aqueous solvent completely from the non-aqueous electrolyte solution which is a target of the heating treatment.

The content of the compound represented by formula (1) (if two or more kinds are used, the total content) in the polyelectrolyte of the invention is, with respect to total mass of the polyelectrolyte, preferably from 0.01% by mass to 100% by mass, more preferably from 0.01% by mass to 90% by mass, still more preferably from 0.01% by mass to 80% by mass, even more preferably from 0.05% by mass to 50% by mass, and particularly preferably from 0.1% by mass to 20% by mass, although the content is varied in accordance with the form of the polyelectrolyte.

When the compound represented by formula (1) is contained in at least a part of the solid polymeric compound, the content of the compound represented by formula (1) (if two or more kinds are used, the total content) is, with respect to total mass of the solid polymeric compound, preferably from 0.1% by mass to 100% by mass, more preferably from 0.1% by mass to 90% by mass, still more preferably from 0.1% by mass to 80% by mass, even more preferably from 0.5% by mass to 50% by mass, particularly preferably from 1% by mass to 20% by mass.

When the compound represented by formula (1) is contained in the non-aqueous electrolyte solution as one of the components of the gel-type polyelectrolyte, the content of the compound represented by formula (1) (if two or more kinds are used, the total content) is, with respect to total mass of the non-aqueous electrolyte solution, preferably from 0.01% by mass to 50% by mass, more preferably from 0.01% by mass to 20% by mass, still more preferably from 0.01% by mass to 10% by mass, even more preferably from 0.05% by mass to 5% by mass, particularly preferably from 0.1% by mass to 2% by mass.

[Lithium Secondary Battery]

The lithium secondary battery of the invention is constituted to basically include a negative electrode, a positive electrode, and at least one of the non-aqueous electrolyte solution of the invention and the polyelectrolyte of the present invention.

Usually, a separator is provided between the negative electrode and the positive electrode.

(Negative Electrode)

As the negative electrode active material that constitutes the negative electrode, at least one selected from metal lithium, a lithium-containing alloy, a metal or alloy capable of alloying with lithium, an oxide capable of doping and dedoping of lithium ions, transition metal nitrides capable of doping and dedoping of lithium ions, and a carbon material capable of doping and dedoping of lithium ions (these may be used singly, or mixtures including two or more kinds of these may also be used) can be used.

Examples of the metal or alloy capable of alloying with lithium (or lithium ions) include silicon, a silicon alloy, tin, and a tin alloy. Furthermore, lithium titanate is also acceptable.

Among these, a carbon material capable of doping and dedoping of lithium ions is preferred. Examples of such a carbon material include carbon black, activated carbon, a graphite material (artificial graphite or natural graphite), and an amorphous carbon material. The form of the carbon material may be any of a fibrous form, a spherical form, a potato form and a flake form.

Specific examples of the amorphous carbon material include hard carbon, cokes, mesocarbon microbeads (MCMB) calcined at or below 1500° C., and mesophase pitch carbon fibers (MCF).

Examples of the graphite material include natural graphite and artificial graphite. Regarding the artificial graphite, graphitized MCMB, graphitized MCF, and the like are used. Furthermore, compounds containing boron can also be used as the graphite material. Also, as the graphite material, a graphite material coated with a metal such as gold, platinum, silver, copper or tin; a graphite material coated with an amorphous carbon; or a mixture of amorphous carbon and graphite can also be used.

These carbon materials may be used singly, or two or more kinds may also be used as mixtures. The carbon material is particularly preferably a carbon material in which the interplanar spacing d(002) of the (002) plane measured by an X-ray analysis is 0.340 nm or less. Furthermore, the carbon material is also preferably a graphite having a true density of 1.70 g/cm$^3$ or greater, or a highly crystalline carbon material having properties close thereto. When a carbon material such as described above is used, the energy density of the battery can be further increased.

(Positive Electrode)

Examples of the positive electrode active material that constitutes the positive electrode include transition metal oxides or transition metal sulfides, such as $MoS_2$, $TiS_2$, $MnO_2$, and $V_2O_5$; composite oxides composed of lithium and transition metals, such as $LiCoO_2$, $LiMnO_2$, $LiMn_2O_4$, $LiNiO_2$, $LiNi_xCo_{(1-x)}O_2$ [0<X<1], and $LiFePO_4$; and electroconductive polymer materials such as polyaniline, polythiophene, polypyrrole, polyacetylene, polyacene, dimercaptothiadiazole, and a polyaniline composite. Among these, composite oxides composed of lithium and transition metals are particularly preferred. When the negative electrode is formed of lithium metal or a lithium alloy, a carbon material can be used as the positive electrode. Also, a mixture of a composite oxide of lithium and a transition metal with a carbon material can be used as the positive electrode.

The positive electrode active materials described above may be used singly, or two or more kinds may also be used as mixtures. If the positive electrode active material has insufficient electroconductivity, the positive electrode can be constructed by using the positive electrode active material together with an electroconductive aid. Examples of the electroconductive aid include carbon materials such as carbon black, amorphous whiskers, and graphite.

(Separator)

The separator is a membrane which electrically insulates the positive electrode and the negative electrode, and transmits lithium ions, and examples thereof include a porous film and a polymer electrolyte.

As the porous film, a finely porous polymer film is suitably used, and examples of materials of the porous film include polyolefins, polyimides, polyvinylidene fluoride, and polyesters.

Particularly, porous polyolefins are preferred, and specific examples thereof include a porous polyethylene film, a porous polypropylene film, and a multilayer film of a porous polyethylene film and a porous polypropylene film. A porous polyolefin film may also have another resin with excellent thermal stability coated thereon.

Examples of the polymer electrolyte include a polymer having a lithium salt dissolved therein, and a polymer swollen with an electrolyte solution.

The non-aqueous electrolyte solution of the invention may also be used for the purpose of obtaining a polymer electrolyte by swelling a polymer. When the non-aqueous electrolyte solution of the invention is used for this purpose, the polyelectrolyte of the invention is obtained in the form of a gel-type polyelectrolyte as described above.

(Configuration of Battery)

The lithium secondary battery of the invention includes the negative electrode active material, positive electrode active material, and separator described above.

The lithium secondary battery of the invention can adopt various known shapes, and the lithium secondary battery can be formed into a cylindrical shape, a coin shape, a rectangular shape, a film shape, and any other shapes. However, the basic structure of the battery is the same irrespective of the shape, and modifications in design can be applied in accordance with the purpose.

An example of the non-aqueous electrolyte secondary battery of the invention may be a coin battery as illustrated in FIG. 1.

In the coin battery illustrated in FIG. 1, a disc-shaped negative electrode 2, a separator 5 in which a non-aqueous electrolyte solution has been injected, a disc-shaped positive electrode 1, and optionally, spacer plates 7 and 8 made of stainless steel, aluminum or the like, which are laminated in this order, are accommodated between a positive electrode can 3 (hereinafter, also referred to as a "battery can") and a sealing plate 4 (hereinafter, also referred to as a "battery can lid"). The positive electrode can 3 and the sealing plate 4 are sealed by caulking with a gasket 6.

In this example, the non-aqueous electrolyte solution of the invention may be used for the non-aqueous electrolyte solution injected in the separator 5.

In this example, the polyelectrolyte of the invention may be used as a least a part of the separator 5 itself.

Meanwhile, the lithium secondary battery of the invention may be a lithium secondary battery obtained by charging and discharging a lithium secondary battery (a lithium secondary battery before being charged and discharged) which includes a negative electrode, a positive electrode, and at least one of the non-aqueous electrolyte solution of the invention and the polyelectrolyte of the present invention.

That is, the lithium secondary battery of the invention may be a lithium secondary battery (a lithium secondary battery that has been charged and discharged) obtained by first producing a lithium secondary battery before being charged and discharged, which includes a negative electrode, a positive electrode and at least one of the non-aqueous electrolyte solution of the invention and the polyelectrolyte of the present invention, and subsequently charging and discharging one or more times the lithium secondary battery before being charged and discharged.

There are no particular limitations on the use of the lithium secondary battery, and it can be used in various known applications. For example, the lithium secondary battery can be widely utilized in small-sized portable devices as well as in large-sized devices, such as notebook computers, mobile computers, mobile telephones, headphone stereos, video movie cameras, liquid crystal television sets, handy cleaners, electronic organizers, calculators, radios, back-up power supply applications, motors, automobiles, electric cars, motorcycles, electric motorcycles, bicycles, electric bicycles, illuminating devices, game players, time pieces, electric tools, and cameras.

EXAMPLES

Hereinafter, the invention will be specifically described by way of examples. The invention is not limited by the examples. In the examples, "%" and "wt %" denote "% by mass".

Synthesis Example 1

Lithium phosphate (2.0 g) and a solution (12.5%, 56.0 g) of boron trifluoride in diethyl carbonate were mixed, and the mixture was stirred at room temperature for 1 hour. The resultant solution was mixed with deuterated acetonitrile (CD$_3$CN). The resultant mixture was analyzed by $^{19}$F NMR and $^{31}$P NMR. Analysis results are as follows:

In the resultant $^{19}$F NMR spectrum, a signal of BF$_2$ corresponding to the resultant crosslinked moieties, and a signal of BF$_3$ corresponding to the resultant terminal moieties were observed. From the integral ratio between these signals, the ratio between the components was calculated to be BF$_2$:BF$_3$=1:1.2.

From the analysis results, it was confirmed that as the compound represented by formula (1), mixtures in which n in the following Formula (a) was from 1 to 5 (hereinafter referred to also as a "compound (a)") were produced.

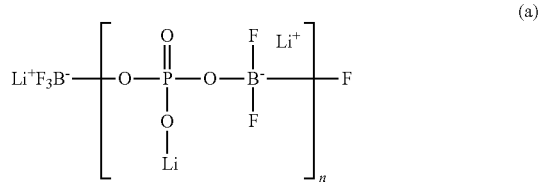

(a)

$^{19}$F NMR (CFCl$_3$=0 ppm, Solvent: CD$_3$CN): δ −143 to −147 (br), −149 to −151 (br)
$^{31}$P NMR (H$_3$PO$_4$=0 ppm, Solvent: CD$_3$CN): δ −18 to −24 (br), −26 to −32 (br)

Synthesis Example 2

Lithium phosphate (2.0 g), lithium fluoride (1.3 g), and a solution (12.5%, 56.0 g) of boron trifluoride in diethyl carbonate were mixed, and the mixture was stirred at room temperature for 1 hour. The resultant solution was mixed with deuterated acetonitrile (CD$_3$CN). The resultant mixture was analyzed by $^{19}$F NMR and $^{31}$P NMR. Analysis results are as follows:

In the resultant $^{19}$F NMR spectrum, a signal of BF$_2$ corresponding to the resultant crosslinked moieties, and a signal of BF$_3$ corresponding to the resultant terminal moieties were observed. From the integral ratio between these signals, the ratio between the components was calculated to be BF$_2$:BF$_3$=1:2.0.

From the analysis results, it was confirmed that as the compound represented by formula (1), mixtures in which n in the following Formula (b) was from 1 to 5 (hereinafter referred to also as a "compound (b)") were produced.

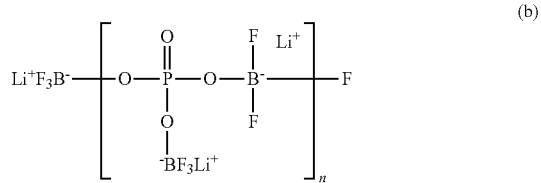

(b)

$^{19}$F NMR (CFCl$_3$=0 ppm, Solvent: CD$_3$CN): δ −144 to −146 (m), −149 to −151 (m)
$^{31}$P NMR (H$_3$PO$_4$=0 ppm, Solvent: CD$_3$CN): δ −18 (m), −21 to −24 (m), −27 to −32 (m)

Synthesis Example 3

Lithium phosphate (2.0 g), a solution (12.5%, 28.0 g) of boron trifluoride in diethyl carbonate, and trimethyl borate (10.7 g) were mixed, and the mixture was stirred at room temperature for 1 hour. The resultant solution was mixed with deuterated acetonitrile (CD$_3$CN). The resultant mixture was analyzed by $^1$H NMR, $^{19}$F NMR, and $^{31}$P NMR. Analysis results are as follows:

In the resultant $^{19}$F NMR spectrum, a signal of BF$_2$ corresponding to the resultant crosslinked moieties, and a signal of BF$_3$ corresponding to the resultant terminal moieties were observed. From the integral ratio between these signals, the ratio between the components was calculated to be BF$_2$:BF$_3$=1:0.6.

From the analysis results, it was confirmed that as compounds each represented by formula (1), mixtures in which n in the following Formula (c) was from 1 to 3 (hereinafter referred to also as a "compound (c)") were produced.

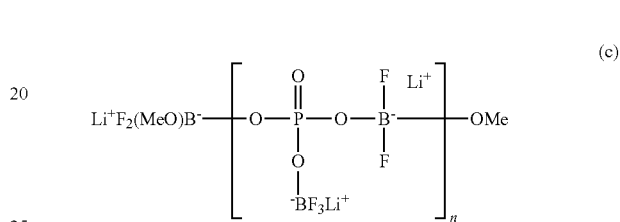

(c)

$^1$H NMR (TMS=0 ppm, Solvent: CD$_3$CN): δ 3.4 to 3.5 (br)
$^{19}$F NMR (CFCl$_3$=0 ppm, Solvent: CD$_3$CN): δ −144 to −146 (m), −149 to −151 (m)
$^{31}$P NMR (H$_3$PO$_4$=0 ppm, Solvent: CD$_3$CN): δ −18 to −24 (br), −26 to −32 (br)

Synthesis Example 4

Lithium methylphosphonate (2.0 g) and a solution (12.5%, 60.0 g) of boron trifluoride in diethyl carbonate were mixed, and the mixture was stirred at room temperature for 1 hour. The resultant solution was mixed with deuterium acetonitrile (CD$_3$CN). The resultant mixture was analyzed by $^1$H NMR, $^{19}$F NMR and $^{31}$P NMR. Analysis results are as follows:

In the resultant $^{19}$F NMR spectrum, a signal of BF$_2$ corresponding to the resultant crosslinked moieties, and a signal of BF$_3$ corresponding to the resultant terminal moieties were observed. From the integral ratio between these signals, the ratio between the components was calculated to be BF$_2$:BF$_3$=1:1.3.

From the analysis results, it was confirmed that as compounds each represented by formula (1), mixtures in which n in the following Formula (d) was from 1 to 5 (hereinafter referred to also as a "compound (d)") were produced.

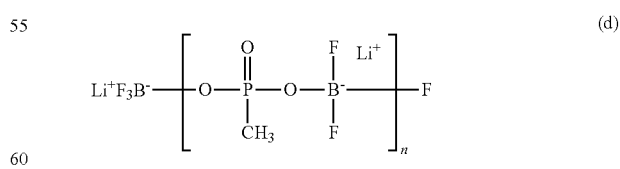

(d)

$^1$H NMR (TMS=0 ppm, Solvent: CD$_3$CN): δ 1.4 to 1.5 (m)
$^{19}$F NMR (CFCl$_3$=0 ppm, Solvent: CD$_3$CN): δ −144 to −146 (m), −149 to −151 (m)
$^{31}$P NMR (H$_3$PO$_4$=0 ppm, Solvent: CD$_3$CN): δ −25 to −28 (br)

Example 1

A lithium secondary battery was made by the following procedure.

<Preparation of Negative Electrode>

20 parts by mass of artificial graphite, 80 parts by mass of natural graphite-based graphite, 1 part by mass of carboxymethyl cellulose, and 2 parts by mass of a SBR latex were kneaded in water solvent, and thus a negative electrode mixture slurry in a paste form was prepared.

Next, this negative electrode mixture slurry was applied on a strip-shaped negative electrode current collector made of a copper foil having a thickness of 18 µm, and the slurry was dried. Subsequently, the assembly was compressed with a roll press, and thus a sheet-like negative electrode composed of a negative electrode current collector and a negative electrode active material layer was obtained. The coating density of the negative electrode active material layer was 10 mg/cm$^2$, and the packing density was 1.5 g/ml.

<Preparation of Positive Electrode>

90 parts by mass of $LiCoO_2$, 5 parts by mass of acetylene black, and 5 parts by mass of polyvinylidene fluoride were kneaded in N-methylpyrrolidinone as a solvent, and thus a positive electrode mixture slurry in a paste form was prepared.

Next, this positive electrode mixture slurry was applied on a strip-shaped positive electrode current collector made of an aluminum foil having a thickness of 20 and the slurry was dried. Subsequently, the assembly was compressed with a roll press, and thus a sheet-like positive electrode composed of a positive electrode current collector and a positive electrode active material layer was obtained. The coating density of the positive electrode active material layer was 30 mg/cm$^2$, and the packing density was 2.5 g/ml.

<Preparation of Non-aqueous Electrolyte Solution>

Ethylene carbonate (EC), dimethyl carbonate (DMC) and methyl ethyl carbonate (EMC) was mixed at proportions of 1:1:1 (mass ratio) as a non-aqueous solvent and thus obtained a mixed solvent.

To the mixed solvent thus obtained, $LiPF_6$ as an electrolyte was dissolved such that the electrolyte concentration in the finally obtainable non-aqueous electrolyte solution would be 1 mol/L.

To the mixed solvent thus obtained, the compound (a) was added as an additive such that the content thereof with respect to the total mass of the finally obtained non-aqueous electrolyte solution would be 0.5 wt %, and thus a non-aqueous electrolyte solution was obtained.

<Preparation of Coin Battery>

The negative electrode described above was punched into a disc form having a diameter of 14 mm, while the positive electrode described above was punched into a disc form having a diameter of 13 mm, and thus coin-shaped electrodes (a negative electrode and a positive electrode) were obtained. Furthermore, a microporous polyethylene film having a thickness of 20 µm was punched into a disc form having a diameter of 17 mm, and thus a separator was obtained.

The coin-shaped negative electrode, the separator and the coin-shaped positive electrode thus obtained were laminated in this order inside a battery can (size 2032) made of stainless steel, and 20 µl of the non-aqueous electrolyte solution was injected therein to impregnate the separator, the positive electrode, and the negative electrode.

Furthermore, an aluminum plate (thickness: 1.2 mm, diameter: 16 mm) and a spring were mounted on the positive electrode, a gasket made of polypropylene was inserted, and the battery was sealed by caulking with the battery can lid. Thus, a coin type lithium secondary battery (hereinafter, may be referred to as a test battery) having a diameter of 20 mm and a height of 3.2 mm and having the configuration illustrated in FIG. 1 was prepared.

The coin battery (a test battery) thus obtained was subjected to the following measurements.

[Evaluation Methods]

<Initial Characteristics of Battery: Measurement of Initial Battery Resistance>

The coin battery was charged at a constant voltage of 4.0 V, then the charged coin battery was cooled to −20° C. in a constant temperature chamber, discharged at a constant current of 0.2 mA at −20° C., and the electric potential decrease in 10 seconds after initiation of discharge was measured, thereby determining the direct current resistance [Ω] of the coin battery, and the obtained value was recorded as the initial resistance value [Ω] (−20° C.).

The initial resistance value [Ω] (−20° C.) of the coin battery of Comparative Example 1 described below was also measured in the same manner.

From these results, using the following formula, the "initial battery resistance [%]", which is the initial resistance value (relative value; %) in Example 1 relative to the initial resistance value [Ω] (−20° C.) in Comparative Example 1 indexed as 100%, was determined.

The obtained results are shown in Table 1.

Initial battery resistance [%]=("initial resistance value [Ω] (at −20° C.) in Example 1"/"initial resistance value [Ω] (at −20° C.) in Comparative Example 1")×100 [%]

<Initial Characteristics of Battery: Measurement of Initial Discharge Capacity and First-cycle Efficiency>

The coin-shaped lithium secondary battery was subjected to 10 cycles in each of which the battery was electrically charged at a constant current of 1 mA and a constant voltage of 4.2 V, and then electrically discharged to 2.85 V at a constant current of 1 mA. At this time, from the charge capacity [mAh] of the battery at the first cycle, and the discharge capacity [mAh] at the first cycle (initial discharge capacity), the first-cycle charge-discharge efficiency (first-cycle efficiency) was calculated in accordance with the following expression:

First-cycle efficiency [%]=("discharge capacity [mAh] at the first cycle"/"charge capacity [mAh] of the battery at the first cycle")×100

Also about the coin-shaped lithium secondary battery of Comparative Example 1, which will be described later, the same measurement was made. On the basis of the measurement result, the first-cycle efficiency [%] was calculated.

On the basis of these results, the initial discharge capacity (relative value; %) in Example 1 relative to the initial discharge capacity in Comparative Example 1 indexed as 100% and the initial efficiency (relative value; %) in Example 1 relative to the initial efficiency in Comparative Example 1 indexed as 100% were determined respectively.

The obtained results are shown in Table 1.

Example 2

A non-aqueous electrolyte solution was prepared in the same manner as Example 1 except that the compound (a) was changed to the compound (b) having the same mass as the compound (a). The preparation and evaluation of a battery were also made in the same manner as Example 1. The obtained results are shown in Table 1.

Example 3

A non-aqueous electrolyte solution was prepared in the same manner as Example 1 except that instead of the compound (a), the compound (b) was added to set the content thereof in the non-aqueous electrolyte solution, which was finally produced, to 1.0%. The preparation and evaluation of a battery were also made in the same manner as Example 1. The obtained results are shown in Table 1.

Example 4

A non-aqueous electrolyte solution was prepared in the same manner as Example 1 except that the compound (a) was changed to the compound (c) having the same mass as the compound (a). The preparation and evaluation of a battery were also made in the same manner as Example 1. The obtained results are shown in Table 1.

Example 5

A non-aqueous electrolyte solution was prepared in the same manner as Example 1 except that the compound (a) was changed to the compound (d) having the same mass as the compound (a). The preparation and evaluation of a battery were also made in the same manner as Example 1. The obtained results are shown in Table 1.

Example 6

A non-aqueous electrolyte solution was prepared in the same manner as Example 1 except that the addition amount of the compound (a) was changed to set the content thereof in the non-aqueous electrolyte solution, which was finally produced, to 10%. The preparation of a battery was also made in the same manner as Example 1.

Next, the battery produced as described above was heated at 60° C. for 3 hours to be subjected to gelatinizing treatment for the non-aqueous electrolyte solution.

About the gelatinizing-treatment-subjected battery, the same evaluations as in Example 1 were made.

The obtained results are shown in Table 1.

The evaluated battery was dismantled. It was confirmed that the non-aqueous electrolyte solution was gelatinized. This gelatinization is believed to be due to the formation of a polymeric compound (polyelectrolyte) as a condensate of the compound (a) by the above heating (at 60° C. for 3 hours).

Example 7

A non-aqueous electrolyte solution was prepared in the same manner as Example 5 except that the addition amount of the compound (d) was changed to set the content thereof in the non-aqueous electrolyte solution, which was finally produced, to 10%. The preparation of a battery was also made in the same manner as Example 5.

Next, the battery produced as described above was heated at 60° C. for 3 hours to be subjected to gelatinizing treatment for the non-aqueous electrolyte solution.

About the gelatinizing-treatment-subjected battery, the same evaluations as in Example 5 were made.

The obtained results are shown in Table 1.

The evaluated battery was dismantled. It was confirmed that the non-aqueous electrolyte solution was gelatinized. This gelatinization is believed to be due to the formation of a polymeric compound (polyelectrolyte) as a condensate of the compound (d) by the above heating (at 60° C. for 3 hours).

Comparative Example 1

A non-aqueous electrolyte solution was prepared in the same manner as Example 1 except that the compound (a) was not added. The preparation and evaluation of a battery were also made in the same manner as Example 1. The obtained results are shown in Table 1.

TABLE 1

| | Compound represented by formula (1) | | Initial characteristics | | |
|---|---|---|---|---|---|
| | Compound No. | Content (wt %) | Initial battery resistance (%) | First-cycle efficiency (%) | Initial discharge capacity (%) |
| Example 1 | (a) | 0.5 | 71 | 99.8 | 99 |
| Example 2 | (b) | 0.5 | 63 | 99.8 | 99 |
| Example 3 | (b) | 1.0 | 58 | 99.9 | 100 |
| Example 4 | (c) | 0.5 | 68 | 99.7 | 98 |
| Example 5 | (d) | 0.5 | 74 | 99.3 | 100 |
| Example 6 | (a) | 10.0 | 82 | 99.6 | 100 |
| Example 7 | (d) | 10.0 | 88 | 99.5 | 99 |
| Comparative Example 1 | None | | 100 | 100 | 100 |

From the results shown in Table 1, it has been confirmed that the use of a compound represented by formula (1) as an additive (each of Examples 1 to 5), or as a polyelectrolyte (each of Examples 6 and 7) makes it possible to decrease the resultant battery in initial battery resistance (that is, to improve the battery in initial resistance characteristic) while maintaining the first-cycle efficiency and the initial discharge capacity of the battery.

The entire disclosure of Japanese Patent Application No. 2013-092924 filed on Apr. 25, 2013 is incorporated in this specification by reference.

All publications, patent applications and technical standards mentioned in this specification are herein incorporated by reference to the same extent as if each individual publication, patent application, or technical standard was specifically and individually indicated to be incorporated by reference.

The invention claimed is:

1. A non-aqueous electrolyte solution for a battery, comprising a compound represented by the following formula (1):

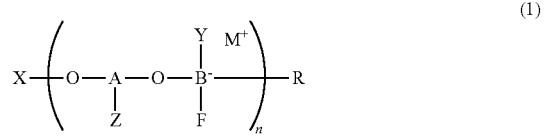

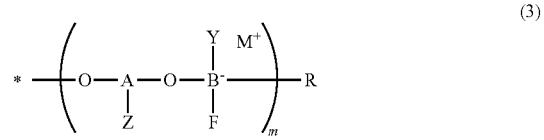

-continued

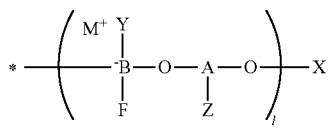
(4)

wherein, in formulae (1) to (4), each A represents a phosphorus atom or P=O; each R represents a hydrogen atom, a halogen atom, an alky group, an aryl group, an alkoxy group, or an aryloxy group; each X represents a hydrogen atom, an alkyl group, an aryl group, an alkali metal atom, or a group represented by formula (2); each Y represents a hydrogen atom, a halogen atom, an alkyl group, an aryl group, an alkoxy group, an aryloxy group, or a group represented by formula (3); each Z represents a hydrogen atom, an alkyl group, an aryl group, or an $OZ^1$ group wherein $Z^1$ represents a hydrogen atom, an alkyl group, an aryl group, an alkali metal atom, a group represented by formula (2), or a group represented by formula (4); each M represents an alkali metal atom; n represents an integer of 1 or more, m represents an integer of 1 or more, and l represents an integer of 1 or more, provided that a sum of n, m, and l in one molecule of the compound represented by formula (1) is an integer from 1 to 200; and in formulae (2) to (4), each * represents a position of bonding.

2. The non-aqueous electrolyte solution for a battery according to claim 1, wherein each of A in formula (1), A in formula (3), and A in formula (4) is P=O.

3. The non-aqueous electrolyte solution for a battery according to claim 1, wherein the sum of n, m, and l in one molecule of the compound represented by formula (1) is an integer from 1 to 30.

4. The non-aqueous electrolyte solution for a battery according to claim 1, wherein n in formula (1) is an integer from 1 to 10; and each of Y in formula (1) and Y in formula (2) is independently a hydrogen atom, a halogen atom, an alkyl group, an aryl group, an alkoxy group, or an aryloxy group; and Z in formula (1) is a hydrogen atom, an alkyl group, an aryl group, or an $OZ^1$ group, wherein $Z^1$ is a hydrogen atom, an alkyl group, an aryl group, an alkali metal atom, or a group represented by formula (2).

5. The non-aqueous electrolyte solution for a battery according to claim 1, wherein each of Z in formula (1), Z in formula (3), and Z in formula (4) is the $OZ^1$ group.

6. A compound represented by the following formula (1):

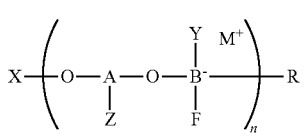
(1)

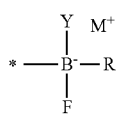
(2)

-continued

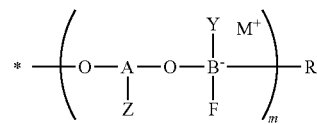
(3)

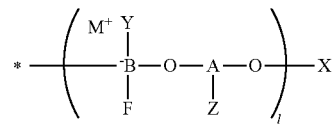
(4)

wherein, in formulae (1) to (4), each A represents a phosphorus atom or P=O; each R represents a hydrogen atom, a halogen atom, an alky group, an aryl group, an alkoxy group, or an aryloxy group; each X represents a hydrogen atom, an alkyl group, an aryl group, an alkali metal atom, or a group represented by formula (2); each Y represents a hydrogen atom, a halogen atom, an alkyl group, an aryl group, an alkoxy group, an aryloxy group, or a group represented by formula (3); each Z represents a hydrogen atom, an alkyl group, an aryl group, or an $OZ^1$ group wherein $Z^1$ represents a hydrogen atom, an alkyl group, an aryl group, an alkali metal atom, a group represented by formula (2), or a group represented by formula (4); each M represents an alkali metal atom; n represents an integer of 1 or more, m represents an integer of 1 or more, and l represents an integer of 1 or more, provided that a sum of n, m, and l in one molecule of the compound represented by formula (1) is an integer from 1 to 200; and in formulae (2) to (4), each * represents a position of bonding.

7. The compound according to claim 6, wherein each of A in formula (1), A in formula (3), and A in formula (4) is P=O.

8. The compound according to claim 6, wherein the sum of n, m, and l in one molecule of the compound is an integer from 1 to 30.

9. The compound according to claim 6, wherein n in formula (1) is an integer from 1 to 10; and each of Y in formula (1) and Y in formula (2) is independently a hydrogen atom, a halogen atom, an alkyl group, aryl group, an alkoxy group, or an aryloxy group; and Z in formula (1) is a hydrogen atom, an alkyl group, an aryl group, or an $OZ^1$ group, wherein $Z^1$ is a hydrogen atom, an alkyl group, an aryl group, an alkali metal atom, or a group represented by formula (2).

10. The compound according to claim 6, wherein each of Z in formula (1), Z in formula (3), and Z in formula (4) is the $OZ^1$ group.

11. A polyelectrolyte, comprising a compound represented by the following formula (1):

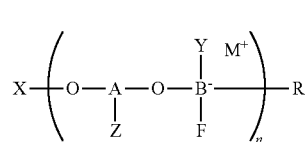
(1)

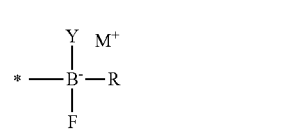
(2)

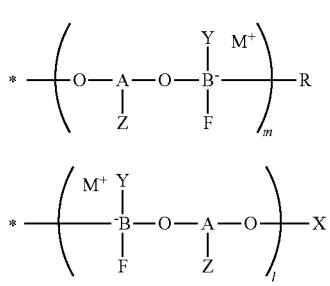

wherein, in formulae (1) to (4), each A represents a phosphorus atom or P=O; each R represents a hydrogen atom, a halogen atom, an alky group, an aryl group, an alkoxy group, or an aryloxy group; each X represents a hydrogen atom, an alkyl group, an aryl group, an alkali metal atom, or a group represented by formula (2); each Y represents a hydrogen atom, a halogen atom, an alkyl group, an aryl group, an alkoxy group, an aryloxy group, or a group represented by formula (3); each Z represents a hydrogen atom, an alkyl group, an aryl group, or an $OZ^1$ group wherein $Z^1$ represents a hydrogen atom, an alkyl group, an aryl group, an alkali metal atom, a group represented by formula (2), or a group represented by formula (4); each M represents an alkali metal atom; n represents an integer of 1 or more, m represents an integer of 1 or more, and l represents an integer of 1 or more, provided that a sum of n, m, and l in one molecule of the compound represented by formula (1) is an integer from 1 to 200; and in formulae (2) to (4), each * represents a position of bonding.

12. The polyelectrolyte according to claim 11, wherein each of A in formula (1), A in formula (3), and A in formula (4) is P=O.

13. The polyelectrolyte according to claim 11, wherein each of Z in formula (1), Z in formula (3), and Z in formula (4) is the $OZ^1$ group.

14. A lithium secondary battery, comprising: a positive electrode; a negative electrode including, as a negative electrode active material, at least one selected from the group consisting of metal lithium, a lithium-containing alloy, a metal or alloy capable of alloying with lithium, an oxide capable of doping and dedoping of lithium ions, a transition metal nitride capable of doping and dedoping of lithium ions, and a carbon material capable of doping and dedoping of lithium ions; and the non-aqueous electrolyte solution for a battery according to claim 1.

15. A lithium secondary battery, obtained by charging and discharging a lithium secondary battery comprising: a positive electrode; a negative electrode including, as a negative electrode active material, at least one selected from the group consisting of metal lithium, a lithium-containing alloy, a metal or alloy capable of alloying with lithium, an oxide capable of doping and dedoping of lithium ions, a transition metal nitride capable of doping and dedoping of lithium ions, and a carbon material capable of doping and dedoping of lithium ions; and the non-aqueous electrolyte solution for a battery according to claim 1.

16. A lithium secondary battery, comprising: a positive electrode; a negative electrode including, as a negative electrode active material, at least one selected from the group consisting of metal lithium, a lithium-containing alloy, a metal or alloy capable of alloying with lithium, an oxide capable of doping and dedoping of lithium ions, a transition metal nitride capable of doping and dedoping of lithium ions, and a carbon material capable of doping and dedoping of lithium ions; and the polyelectrolyte according to claim 11.

17. A lithium secondary battery, obtained by charging and discharging a lithium secondary battery comprising: a positive electrode; a negative electrode including, as a negative electrode active material, at least one selected from the group consisting of metal lithium, a lithium-containing alloy, a metal or alloy capable of alloying with lithium, an oxide capable of doping and dedoping of lithium ions, a transition metal nitride capable of doping and dedoping of lithium ions, and a carbon material capable of doping and dedoping of lithium ions; and the polyelectrolyte according to claim 11.

* * * * *